United States Patent
Curtin et al.

(10) Patent No.: US 12,320,136 B2
(45) Date of Patent: *Jun. 3, 2025

(54) MEDICAL DEVICE DOCKING STATION

(71) Applicant: Physio-Control, Inc., Redmond, WA (US)

(72) Inventors: Barry D. Curtin, Seattle, WA (US); Alexander Hamilton, Seattle, WA (US); Kristina Edmonson, Woodinville, WA (US); David Andrews, Redmond, WA (US); Christopher G. Alviar, Seattle, WA (US); Neal Stanley Clark, Snohomish, WA (US); Benjamin Danziger, Kenmore, WA (US); Christopher William Egbert, Redmond, WA (US); Jason Fouts, Bothell, WA (US); Matthew Malone, Snohomish, WA (US); Joshua Berndt, Redmond, WA (US); Brigitta M. Suwandana, Woodinville, WA (US); Jeremy Edward Brummett, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/422,894

(22) Filed: Jan. 25, 2024

(65) Prior Publication Data

US 2024/0159068 A1 May 16, 2024

Related U.S. Application Data

(63) Continuation of application No. 17/214,211, filed on Mar. 26, 2021, now Pat. No. 11,920,361.

(Continued)

(51) Int. Cl.
*E04H 1/12* (2006.01)
*A61N 1/39* (2006.01)
(Continued)

(52) U.S. Cl.
CPC ......... *E04H 1/1216* (2013.01); *A61N 1/3968* (2013.01); *A61N 1/3975* (2013.01);
(Continued)

(58) Field of Classification Search
CPC .. E04H 1/1216; A61N 1/3968; A61N 1/3975; B60P 1/286; B60P 1/6409; B60R 15/00;
(Continued)

(56) References Cited

U.S. PATENT DOCUMENTS 6,183,417 B1 2/2001 Geheb et al.
6,594,146 B2 7/2003 Frangesch et al.
(Continued)

FOREIGN PATENT DOCUMENTS

DE 202017102768 U1 7/2017
EP 2894540 A1 7/2015
(Continued)

OTHER PUBLICATIONS

Office Action for U.S. Appl. No. 17/214,211, mailed on Jul. 7, 2023, Curtin, "Medical Device Docking Station", 8 pages.

*Primary Examiner* — Jean F Duverne
(74) *Attorney, Agent, or Firm* — Lee & Hayes, P.C.

(57) ABSTRACT

A docking station for a medical device is described. In some examples, the docking station includes a frame and a base plate coupled to the frame. At least a portion of the base plate is coupled to a lower portion of the frame. In some examples, an electronic connector of the docking station is configured to couple to the medical device and to provide power to the medical device when the medical device is docked to the docking station. In some examples, a docking (Continued)

mechanism is coupled to an upper portion of the frame and configured to retain the medical device.

20 Claims, 16 Drawing Sheets

Related U.S. Application Data

(60) Provisional application No. 63/001,109, filed on Mar. 27, 2020.

(51) Int. Cl.
| | | |
|---|---|---|
| *B60P 1/28* | (2006.01) | |
| *B60P 1/64* | (2006.01) | |
| *B60R 15/00* | (2006.01) | |
| *H01R 13/631* | (2006.01) | |
| *H01R 33/76* | (2006.01) | |
| *H01R 33/90* | (2006.01) | |
| *H01R 33/97* | (2006.01) | |
| *H02J 7/00* | (2006.01) | |

(52) U.S. Cl.
CPC .............. *B60P 1/286* (2013.01); *B60P 1/6409* (2013.01); *B60R 15/00* (2013.01); *H01R 33/765* (2013.01); *H01R 33/90* (2013.01); *H01R 33/97* (2013.01); *H01R 13/631* (2013.01); *H01R 2201/12* (2013.01); *H01R 2201/26* (2013.01); *H02J 7/0044* (2013.01)

(58) Field of Classification Search
CPC ...... H01R 33/765; H01R 33/90; H01R 33/97; H01R 13/631; H01R 2201/12; H01R 2201/26; H02J 7/0044
See application file for complete search history.

(56) References Cited

U.S. PATENT DOCUMENTS

| | | | |
|---|---|---|---|
| 6,865,418 | B2 | 3/2005 | Merry |
| D625,015 | S | 10/2010 | Hansen et al. |
| 11,920,361 | B2 * | 3/2024 | Curtin ................... B60P 1/286 |
| 2003/0167074 | A1 * | 9/2003 | Merry ................. A61N 1/3968 |
| | | | 607/5 |
| 2013/0046197 | A1 | 2/2013 | Dlugos, Jr. et al. |
| 2021/0218207 | A1 | 7/2021 | Curtin et al. |

FOREIGN PATENT DOCUMENTS

| | | | |
|---|---|---|---|
| WO | WO-2004093979 A1 * | 11/2004 | ............ A61B 5/01 |
| WO | WO2014160838 | 10/2014 | |

* cited by examiner

MEDICAL DEVICE DOCKING STATION

CROSS-REFERENCE TO RELATED APPLICATION

This application is a continuation of U.S. patent application Ser. No. 17/214,211, filed on Mar. 26, 2021, which claims benefit of U.S. Provisional Application No. 63/001,109, filed on Mar. 27, 2020, titled "Medical Device Docking Station", which are incorporated by reference herein in their entirety.

BACKGROUND

A monitor-defibrillator is a portable, life-saving piece of equipment that is brought to a patient to monitor and treat the patient during an emergency medical event. As the patient is transported from the site of the emergency medical event, such as in an ambulance, the monitor-defibrillator often remains with the patient to continue monitoring and treatment during transport, until the patient arrives at a care facility. However, an unsecured monitor-defibrillator used within a moving vehicle can present a hazard or nuisance to the patient, rescuers, or others caring for the patient.

Additionally, portable medical devices, such as monitor-defibrillators, typically include a direct current (DC) power source, such as batteries, to provide power to electronic components of the medical device. Some DC batteries are configured to be recharged by coupling the medical device to an external power source, such as an alternating current (AC) power source. In a vehicle, such as an ambulance, a connection to an external power source may not be positioned near the patient, making it difficult to have the portable medical device connected to the external power source while positioned in a convenient manner for treating the patient. For example, if the medical device is not positioned near the patient due to its connection to an external power source, the rescuers' treatment of the patient may be hindered because the rescuers may have to break their concentration on the patient to interact with the portable medical device. Additionally, should the portable medical device be operating on battery power and the batteries become depleted during care of the patient, further delays may occur as the rescuers interrupt patient care to connect the portable medical device to the external power source. The disclosure made herein is presented with respect to these and other considerations.

DETAILED DESCRIPTION

Figure 1:
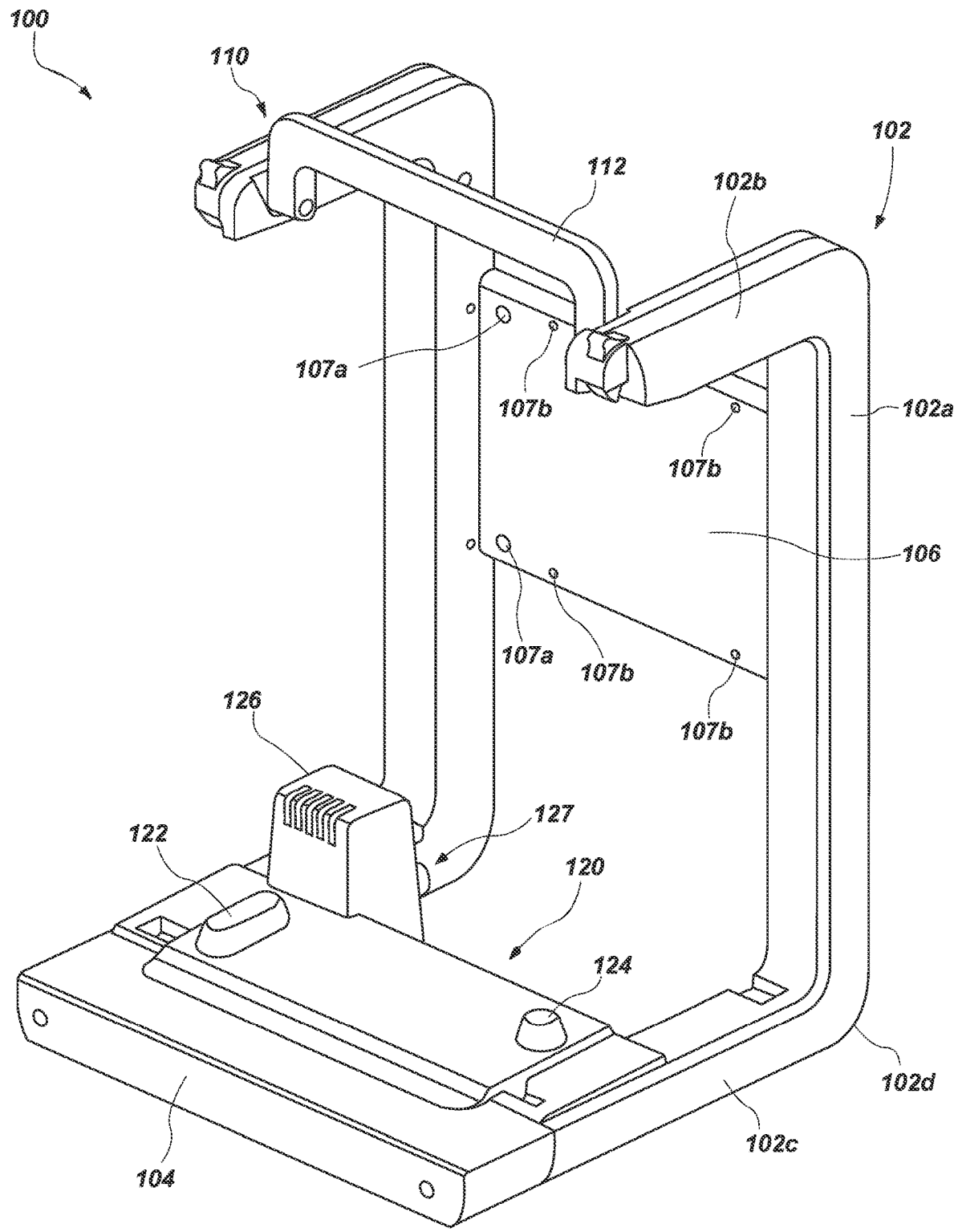
FIG. 1 illustrates a front perspective view of an example medical device docking station.
Figure 2:
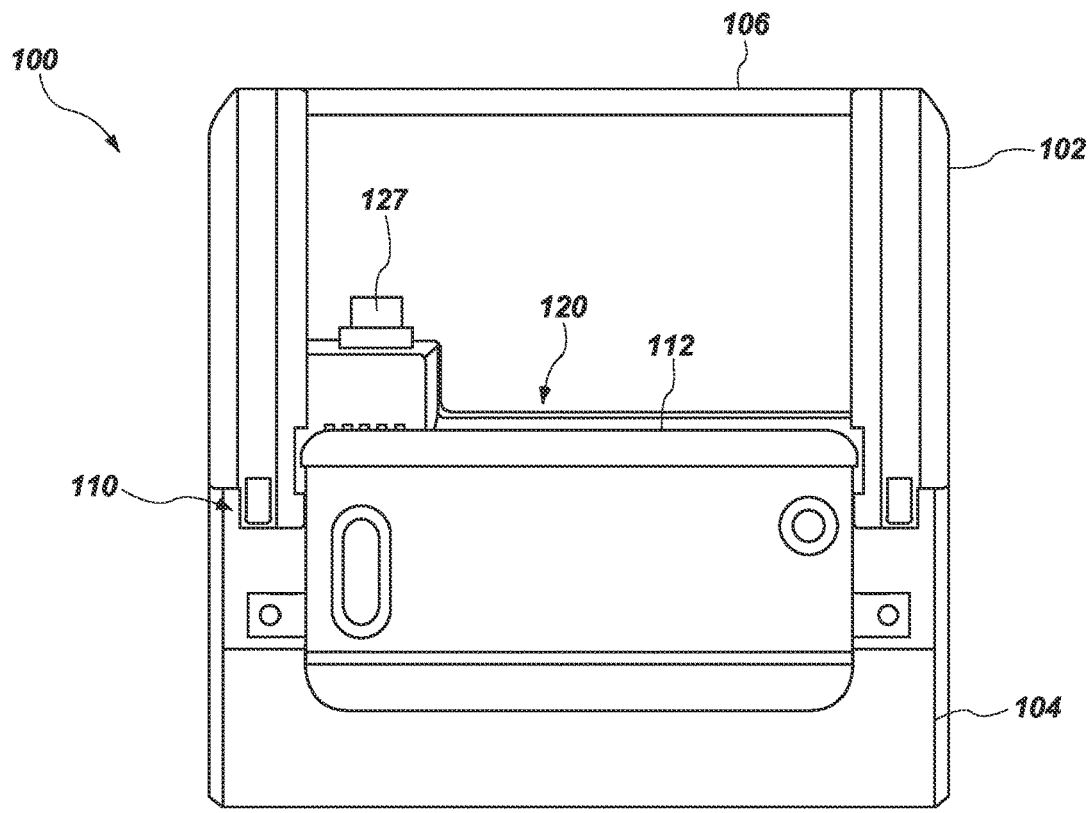
FIG. 2 illustrates a top plan view of the example docking station depicted in FIG. 1.

Portable medical devices provide life-saving monitoring and treatment capabilities that assist a rescuer who is attending to a patient. A "rescuer," as used herein, is the person operating the disclosed medical devices and treating the patient; however, the term "rescuer" includes any user, such as a bystander or other user, whether trained or untrained to use such medical devices. The portability of a medical device allows the medical device to be positioned near a patient, as needed by the rescuer, both while treating the patient at the scene of an emergency medical event or treating the patient within a moving vehicle during patient transport from the emergency medical event. Unsecured medical devices (e.g., those that are not retained or otherwise secured to a surface) within a moving vehicle, such as an ambulance, can pose a hazard and/or a nuisance for the vehicle occupants. However, retaining the medical device using ad hoc equipment (e.g., straps, etc.) can make it difficult to both connect the medical device to an external power source and have the medical device positioned conveniently for the rescuer.

The disclosure provides examples of a medical device docking station that is configured to, among other things, securely retain a medical device. When the docking station is securely positioned within a vehicle, the docking station prevents unintentional movement of the medical device relative to the vehicle. The docking station allows for efficient docking of the medical device to the docking station and for efficient removal of the medical device from the docking station. As used herein, "docking" the medical device to the docking station means coupling the medical device to the docking station in any suitable fashion, such as placing the medical device on or in the docking station, whereby the medical device is retained by the docking station once it is docked to the docking station. Furthermore, the docking station allows for positioning the medical device to maximize rescuer ease and comfort during use of the medical device, and to minimize delays in patient care. In certain examples, docking the medical device to the docking station also electrically connects the medical device to an external power source, which provides electrical power to the docked medical device. In some examples, the electrical connection that is established upon docking the medical device to the docking station connects the medical device to an external device(s), network(s), and/or system, such as remote computing device(s), network(s), and/or system(s), which allows the medical device to communicate with the external device(s), network(s), and/or system(s).

In some examples, the medical device that is configured to dock at the disclosed docking station is a defibrillator, such as a monitor-defibrillator used by emergency medical services (EMS) teams to monitor and treat patients during emergency medical events. Such monitor-defibrillators are portable devices that are physically moved to a position near the patient experiencing the emergency medical event and then transported with the patient to a medical facility, such as a hospital. For example, a patient experiencing a cardiac event undergoes monitoring and potentially treatment, such as cardiopulmonary resuscitation (CPR), defibrillation therapy, drug therapy, and/or other therapies until the patient is in a condition deemed sufficient to transport the patient to a hospital for further care. To perform this monitoring and treatment, EMS teams often connect the patient to a portable monitor-defibrillator upon arrival at the emergency scene. Once the patient's condition is approved for transport, the patient and the monitor-defibrillator are moved together into an ambulance with the monitor-defibrillator still connected to the patient to facilitate continued monitoring and possibly further treatment. Once the patient and the monitor-defibrillator are inside the ambulance, the EMS team continues to monitor and possibly administer treatment to the patient during transport.

The portable monitor-defibrillator in this cardiac event example is secured within the ambulance using the disclosed docking station to avoid the danger of the monitor-defibrillator colliding with the patient or an EMS team member, and to allow the EMS team to easily use the monitor-defibrillator during continued monitoring and treatment of the patient during transport. The medical device disclosed herein may be any suitable medical device or a combination of medical devices, such as an automated external defibrillator (AED), a manual defibrillator, a monitor-defibrillator, other medical devices that couple to the monitor-defibrillator (through wireless or through wired connections), other portable medical devices, or the like. It is to be appreciated that the disclosed docking station is configured to be used with any suitable type of medical devices, and that the docking station may be utilized in any suitable environment, such as within an ambulance or other types of vehicles.

To secure a medical device within a vehicle, such as an ambulance, the medical device is configured to be docked to a docking station disclosed herein. The rescuer docks the medical device to the docking station, and a docking mechanism automatically engages to retain the medical device in or on the docking station. To remove the medical device from the docking station, the rescuer can actuate a handle that, when actuated, disengages the docking mechanism. In some examples, the handle is configured to be actuated using a single hand, which allows the rescuer to easily disengage the docking mechanism and remove the medical device from the docking station. The automatic engagement of the docking mechanism and the disengagement using the handle allows the rescuer to quickly and easily dock the medical device to the docking station and to efficiently remove the medical device from the docking station.

In some examples, the docking station includes an electronic connector that couples the medical device to an external power source and optionally establishes a communications connection that allows the medical device to communicate with an external device(s), network(s), and/or system. In some examples, the medical device includes a mating electronic connector that interfaces with the electronic connector of the docking station. The docking of the medical device to the docking station causes the mating electronic connector of the medical device to couple to the electronic connector of the docking station. The removal of the medical device from the docking station decouples the mating electronic connector of the medical device from the electronic connector of the docking station. As used herein, the term "couple" may refer to an indirect coupling or a direct coupling between elements. The term "couple," as used herein, may also refer to a removable coupling or a permanent coupling between the elements. Elements are removably coupled if a user or another entity is able to decouple the elements. Elements are permanently coupled if a user or another entity is unable to decouple the elements without destroying or significantly damaging the elements, or without undue effort to dissemble the elements using tools or machinery. As used herein, the term "couple" can be interpreted as connect, attach, join, engage, interface, link, fasten, or bind. Unless otherwise specified herein, the term "couple" is to be interpreted as coupling elements in a mechanical sense, rather than in an electrical sense, for example. Nevertheless, it is to be appreciated that a mechanical coupling of elements may result in an electrical coupling(s) between multiple elements of the system.

In some examples, the coupling between the mating electronic connector of the medical device and the electronic connector of the docking station causes power to be provided to the medical device from an external power source, and optionally establishes other electronic connections, such as communication between the medical device and other external device(s), network(s), or system(s), including other nearby or remote medical device(s), caregiver device(s), computer network(s) or system(s), communication platforms such as Bluetooth®, WiFi, or WiGig or other electronic coupling(s) or communication(s).

FIGS. 1-13 illustrate various views of an example docking station 100. FIGS. 1-6 illustrate views of the docking station 100 without a medical device 150 docked to the docking station 100. FIGS. 7-13 illustrate views of the docking station 100 with a medical device 150 docked to the docking station 100. The example medical device 150 shown in these figures is a defibrillator (e.g., a monitor-defibrillator).

The docking station 100 of FIGS. 1-13 includes a docking mechanism 110 and a base plate 120. The base plate 120 is configured to interface with (e.g., contact, support, etc.) a medical device mounted therein, such as the medical device 150 of FIGS. 7-13. In these examples, the medical device 150 is inserted into or placed onto the docking station 100, and the docking mechanism 110 automatically engages (e.g., grabs, grasps, hooks, etc.) a portion of the medical device 150 to dock the medical device 150 to the docking station 100 and retain the medical device 150. In some examples, the docking mechanism 110 is disposed at an upper portion of the docking station 100 (e.g., at the distal ends of two arms 102b) to engage a top portion of the medical device 150. To remove the medical device 150 from the docking station 100, the rescuer actuates the docking mechanism 110 with an actuator, such as a handle 112. Actuation of the handle 112 causes the docking mechanism 110 to disengage from the portion of the medical device 150. The disengagement of the docking mechanism 110 allows the medical device 150 to be removed from the docking station 100. The docking mechanism 110 is discussed in more detail below with reference to FIG. 18.

In some examples, the docking station 100 includes a base plate 120 that is configured to interface with (e.g., contact, support, etc.) a bottom surface (or base) of the medical device 150 when the medical device 150 is docked to the docking station 100. The example base plate 120 includes positioning guides 122, 124 and an electronic connector 126 that is disposed on (e.g., integrated with) the base plate 120. The positioning guides 122, 124 are each configured to mate with corresponding cavity defined in the bottom surface (or base) of the medical device 150. As the medical device 150 is docked to the docking station 100, the positioning guides 122, 124 engage (e.g., insert into) the corresponding cavities defined in the bottom surface of the medical device 150 to assist with positioning the medical device 150 on the base plate 120. When the medical device 150 is docked to the docking station 100, a mating electronic connector of the medical device 150 engages the electronic connector 126 of the docking station 100 to establish one or more electrical connection(s) between them. Through this or these connection(s), the medical device 150 is connected to an external power source that is configured to supply power to the medical device 150 originating from the external power source, and the medical device 150 optionally establishes a communication connection to transmit data to, and/or receive data from an external device(s), network(s), and/or system(s).

In some examples, the docking station 100 includes the docking mechanism 110, a frame 102, a front plate 104, and a back plate 106. In the example shown in FIGS. 1-13, the frame 102 is substantially C-shaped to fit around the exterior of the medical device 150 or a portion of the medical device 150, such as the back 150b of the medical device 150. For example, the C-shaped frame 102 is configured to fit around the medical device 150 from the rear of the medical device 150. It is to be appreciated that the frame 102 can be any other suitable shape, and the frame 102 may be curved and/or angled to fit around the medical device 150 or a portion thereof. The frame 102 shown in FIGS. 1-13 includes two C-shaped members that that are vertically-oriented and spaced apart from each other, each C-shaped member including a post 102a that is vertically-oriented when the docking station 100 is upright (as shown in FIG. 1), an arm 102b extending orthogonally from a top (e.g., a first, top end) of the post 102a, and a leg 102c extending orthogonally from a bottom (e.g., a second, bottom end) of the post 102a. In some examples, the two posts 102a are both vertical and straight, and, therefore, parallel with each other. Similarly, the arms 102b and the legs 102c, in some examples, are parallel with each other. The posts 102a of the frame 102 are shown in a vertical orientation and spaced apart by roughly the same width as the medical device 150. It is to be appreciated however, that the posts 102a may be in an orientation other than vertical, in some examples. Further, in some examples, the posts 102a are not parallel. In some examples, the posts 102a are angled relative to each other, or the posts 102a may include some curvature. In some examples, the posts 102a are a single integrated member. In other examples, the posts 102a include more than two parallel (or non-parallel) members. Likewise, the arms 102b and the legs 102c, in some examples, are single integrated pieces, or they are separated into multiple arm(s) 102b and multiple leg(s) 102c, including more than two arms 102b and more than two legs 102c. Further, the cross-sectional shape of the posts 102a, the arms 102b, and the legs 102c is shown in a generally rectangular shape, and the corners at the junction between the posts 102a and the arms 102b and legs 102c are depicted as curved corners in FIGS. 1-13. It is to be appreciated, however, that the cross-sectional shape of the posts 102a, the arms 102b, and the legs 102c may be another shape, such as circular (e.g., a circular tube), triangular, square, pentagonal, hexagonal, etc., and the corners where the posts 102a meet the arms 102b and legs 102c may be sharp corners without curvature.

Referring to FIG. 1, the arms 102b of the frame 102 are positioned at first (e.g., top) ends of the posts 102a, and at least a portion of the docking mechanism 110 is positioned between the arms 102b at distal ends of the arms 102b. The legs 102c of the frame 102 are positioned at the second (e.g., bottom) ends of the posts 102a. The second ends of the posts 102a are opposite their first ends. The posts 102a shown in FIGS. 1-13 are each integrated with a portion of the two arms 102b and the two legs 102c, which are linked or joined by a curved portion 102d of the frame 102 to each of the posts 102a. In other examples, the portions of the frame 102 are individual elements that are joined together, and/or the joint(s) or junction(s) between elements of the frame 102 have various profiles other than the curved profile shown, such as a square or angular profile.

In the example of FIGS. 1-13, the frame 102 has two sides that mirror each other. The frame 102 includes a first side and a second side that each have a post 102a, an arm 102b, and a leg 102c. The two sides of the frame 102 are connected together by the handle 112, the front plate 104, the base plate 120, and/or the back plate 106. In some examples, the handle 112 is positioned at or near distal ends of the arms 102b (e.g., the free ends of the arms 102b that are opposite the proximal ends adjoined with the posts 102a from which the arms 102b extend). The handle 112 extends between the arms 102b of the frame 102 to connect the arms 102b of the two sides of the frame 102. Accordingly, the handle 112 is oriented horizontally to span the distance that the two arms 102b are spaced apart. The back plate 106 is positioned on rear surfaces of the posts 102a. The rear surfaces of the posts 102a are opposite front surfaces of the posts 102a from which the arms 102b and legs 102c extend. The back plate 106 is coupled to the posts 102a to connect the posts 102a of the two sides of the frame 102. The front plate 104 is positioned at the distal ends of the legs 102c (e.g., the ends of the legs 102c that are opposite the proximal ends adjoined to the posts 102a from which the legs 102c extend). The front plate 104 is coupled to the distal ends of the legs 102c to connect the legs 102c of the two sides of the frame 102. In some examples, the two sides of the frame 102 are connected in other manners. For example, other features or elements can join the two sides of the frame 102. These other features or elements that join the two sides of the frame 102 can be in addition to or in place of the handle 112, front plate 104, base plate 120, back plate 106, or a combination thereof.

In some examples, the frame 102 has alternative arrangements to those described in reference to FIGS. 1-13, such as a sectional frame 102 formed with an upper section, a middle section, and a lower section. The upper section of this alternative frame 102 includes the arms 102b and the docking mechanism 110 shown in FIGS. 1-13. The middle section of this alternative frame 102 includes the posts 102a, also shown in FIGS. 1-13. The lower section of this alternative frame 102 includes the legs 102c and a front plate 104, also shown in FIGS. 1-13. In this example, the upper, middle and lower sections are connected or joined together to form the frame 102. It is to be appreciated that, even if the C-shaped members of the frame 102 do not include multiple sections that are coupled together (e.g., if the C-shaped members are monolithic parts), the C-shaped frame 102 can be considered to include a middle portion (e.g., the posts 102a), an upper portion (e.g., the arms 102b), and a lower portion (e.g., the legs 102c).

Referring again to FIG. 1, the docking station 100 is configured to be mounted to a surface, such as a counter or shelf within a vehicle. Such mounting of the docking station 100 to a surface secures the docking station 100 during movement of the vehicle and from unintentional impact. The legs 102c of the frame 102 include openings, such as through holes, through which a faster(s) like a screw(s) or a bolt(s) is configured to be inserted to couple the docking station 100 to the surface. Mounting the docking station 100 to the surface secures the docking station 100 to the surface and prevents movement of the docking station 100 with respect to the surface to which it is coupled, such as preventing the unwanted movement of the docking station 100 within the moving vehicle or by unintentional impact.

In some examples, the docking station 100 is configured to be mounted from above so that the docking station 100 hangs below a surface, such as the underside of a cabinet, a ceiling, etc. To secure the docking station 100 in such a manner, the arms 102b of the docking station 100 are configured to be secured to the surface, or an intervening element(s) is used to couple the arms 102b or another portion of the docking station 100 to the surface.

In some examples, the docking station 100 is configured to be releasably mounted to a surface to allow the docking station 100 to be decoupled and removed from the surface or to be repositioned on the same or another surface, as desired. Releasable mounting elements secure the docking station 100 to the surface in a releasable manner. For example, releasable mounting elements include screws, bolts, temporary adhesives, or other releasable mounting elements or systems.

In some examples, an underside or bottom surface of the legs 102c of the frame 102 include features, such as protrusions or openings that engage complementary features of the surface to further secure the docking station 100 to the surface. In an example, openings on the underside of the legs 102c are configured to engage with (e.g., receive) protrusions, such as pins or dowels extending from the surface to position the docking station 100 on the surface and prevent movement of the docking station 100 along the surface. In some examples, the protrusions extending from the surface include locking features, such as a spring-driven catch, to engage with the docking station 100 and secure the docking station 100 to the protrusions on the surface. In some examples, the protrusions extending from the surface are configured to engage (e.g., insert into) the openings defined in the underside of the legs 102c in a non-locking manner to prevent lateral motion of the docking station 100 across the surface while not impeding vertical motion of the docking station 100 from the surface, such as to facilitate quick and easy removal of the docking station 100 from the surface.

Figure 10:
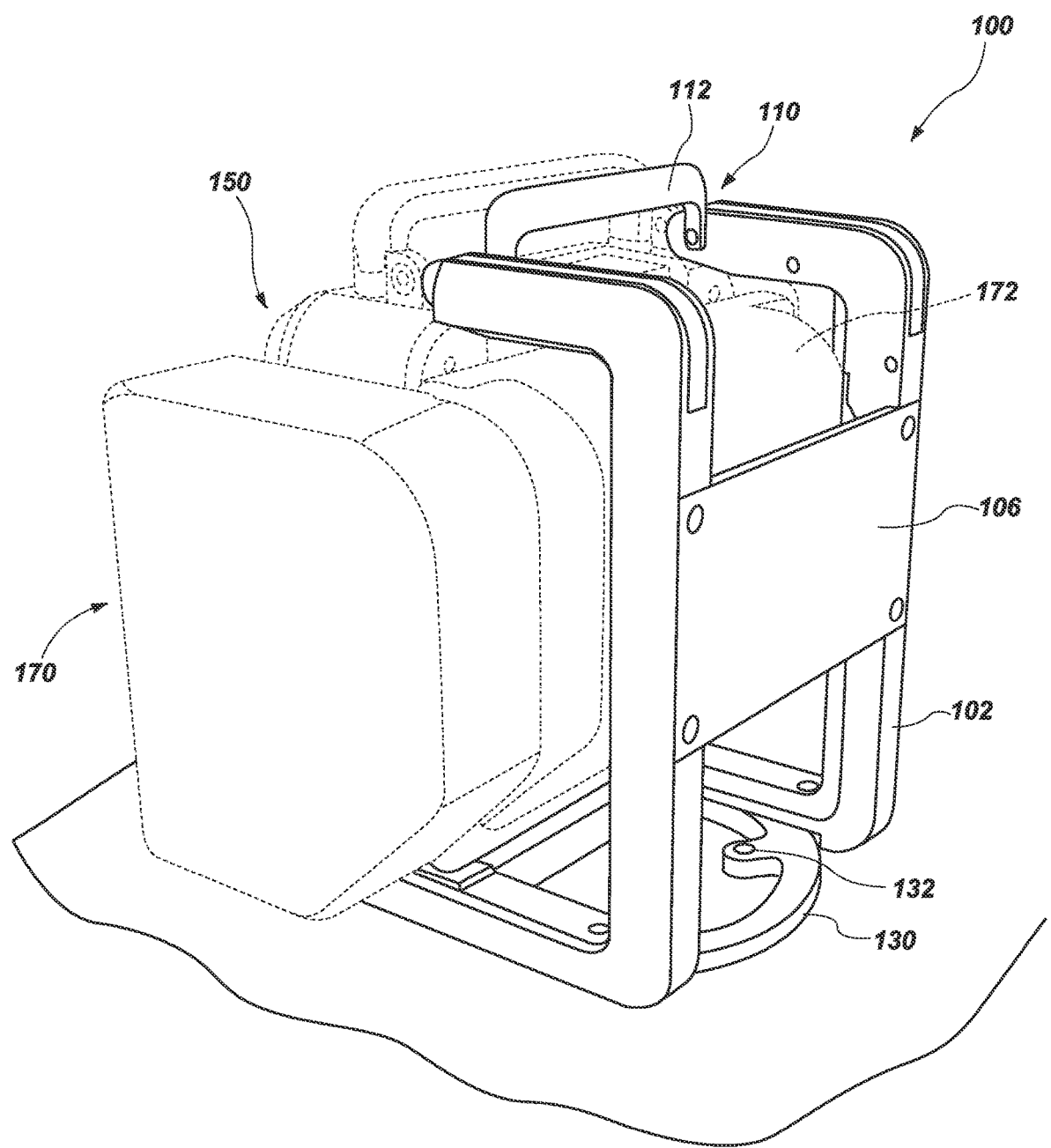
FIG. 10 illustrates a rear perspective view of the example medical device and docking station depicted in FIG. 9.
Figure 11:
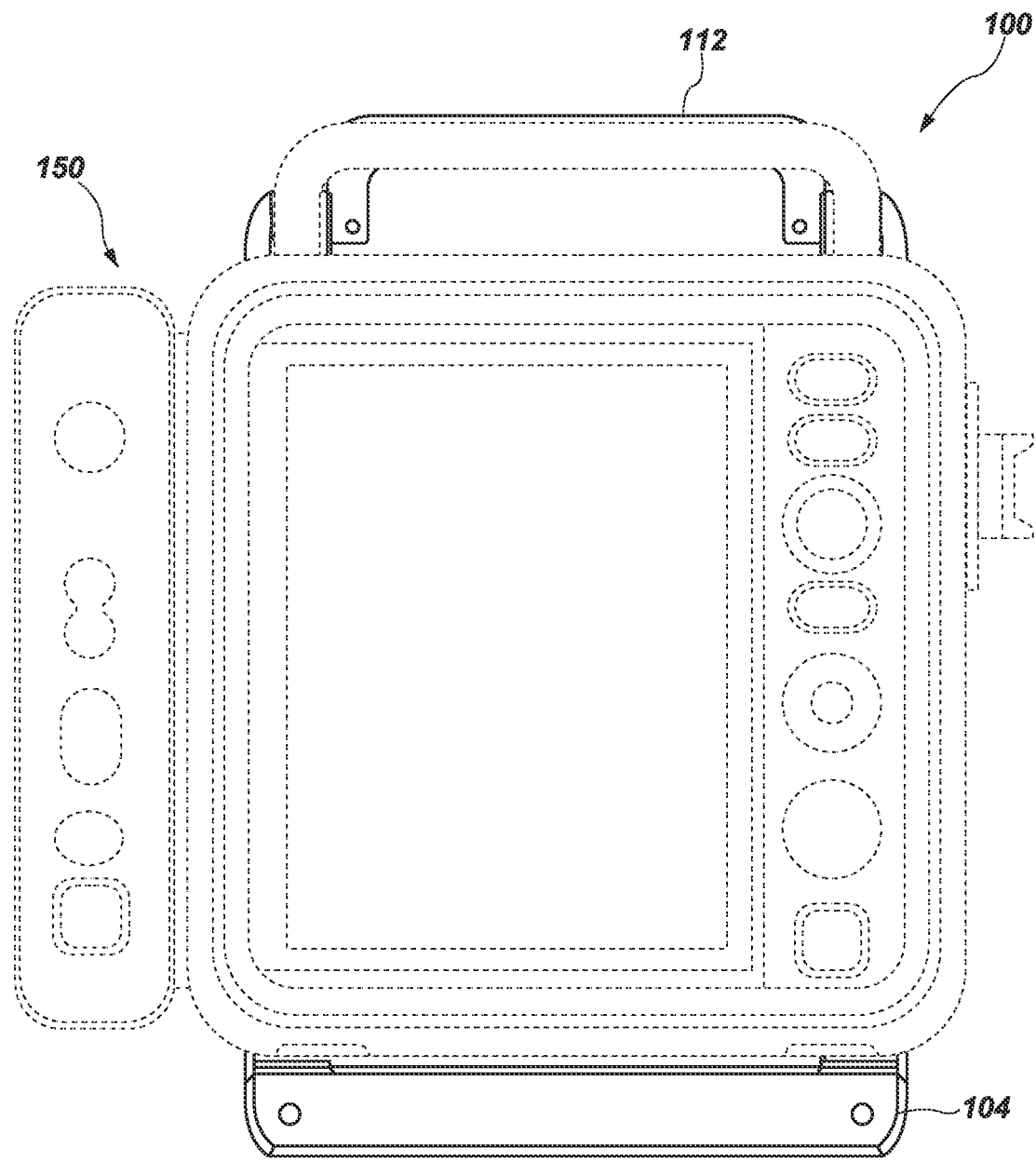
FIG. 11 illustrates a front plan view of the example medical device and docking station depicted in FIG. 7.

In an example, the docking station 100 includes a turntable 130 that is integrated with or coupled to an underside of the frame 102. FIG. 10 shows an example turntable 130 that is coupled to an underside of the legs 102c of the frame 102 and disposed beneath the legs 102c. In some examples, the turntable 130 is coupled to an underside of the base plate 120. In some examples, the turntable 130 includes openings 132 (e.g., through holes) or other attachment elements to allow the turntable 130 to be coupled to the surface on which the docking station 100 rests. In an example, the turntable 130 of the docking station 100 is configured to be coupled to a surface within a vehicle, such as a shelf, cabinet, or countertop, using the openings 132 defined in the turntable 130. To secure the docking station 100 to the surface, fasteners (e.g., screws) are passed through the openings 132 defined in the turntable 130 to engage the surface and couple the turntable 130 and the docking station 100 to the surface.

The turntable 130 allows the docking station 100 to rotate relative to the surface. The rescuer is able to rotate or swivel the docking station 100 so that the retained medical device 150 is viewable in different positions and adjusted, as desired. In some examples, the rotation of the docking station 100 is a clockwise or a counterclockwise rotation about an imaginary vertical axis running through a center of the docking station 100 from top-to-bottom. In some examples, the example turntable 130 includes an element, such as a mechanical stopper or a detent, that limits or prevents unintended rotation of the turntable 130 caused by movement of the vehicle or unintentional impact with the medical device 150 and/or the docking station 100. In an example, the turntable 130 includes a lock that the rescuer engages to prevent further rotation of the turntable 130 and/or the docking station 100 after the turntable 130 and/or docking station 100 is positioned in the desired position or orientation. In another example, the turntable 130 includes multiple, fixed orientations to which the docking station 100 is configured to be rotated. When rotated, the docking station 100 locks into one of the fixed orientations to prevent further rotation beyond the selected fixed orientation. In some examples, an application of force is required to rotate the turntable 130 and/or the docking station 100 from the selected fixed orientation. The force needed to rotate the turntable 130 from the selected fixed orientation can be sufficiently large so that force created by routine movement of the vehicle does not overcome the needed force to cause rotation of the turntable 130 and/or the docking station 100. In an example, the turntable 130 includes one or more detents that are each associated with one of the fixed orientations and require a predetermined amount of force to release the turntable from the fixed orientation associated with one of the detents.

In some examples, the turntable 130 includes a tilt feature to allow the docking station 100 to be tilted relative to the surface on which the turntable 130 rests. In this manner, the rescuer is able to move the medical device 150 in three dimensions by rotating the docking station 100 (e.g., clockwise or counterclockwise) with the turntable 130 and tilting the docking station 100 with the tilt feature of the turntable 130. In an example, the rescuer is able to tilt the docking station 100 to adjust the inclination of the medical device 150 so the medical device 150 is positioned at an angle relative to the surface (e.g., in a reclined or an inclined orientation). This tilt motion allows the rescuer to look downward at the medical device 150 to more easily view a display on the front of the medical device 150. Similarly, the medical device 150 is configured to be tilted to position the display of the medical device 150 at an opposing angle to the inclined position, which is useful if the rescuer is positioned below the level of the display of the medical device 150, such as when the rescuer is sitting down or kneeling next to a patient.

Figure 5:
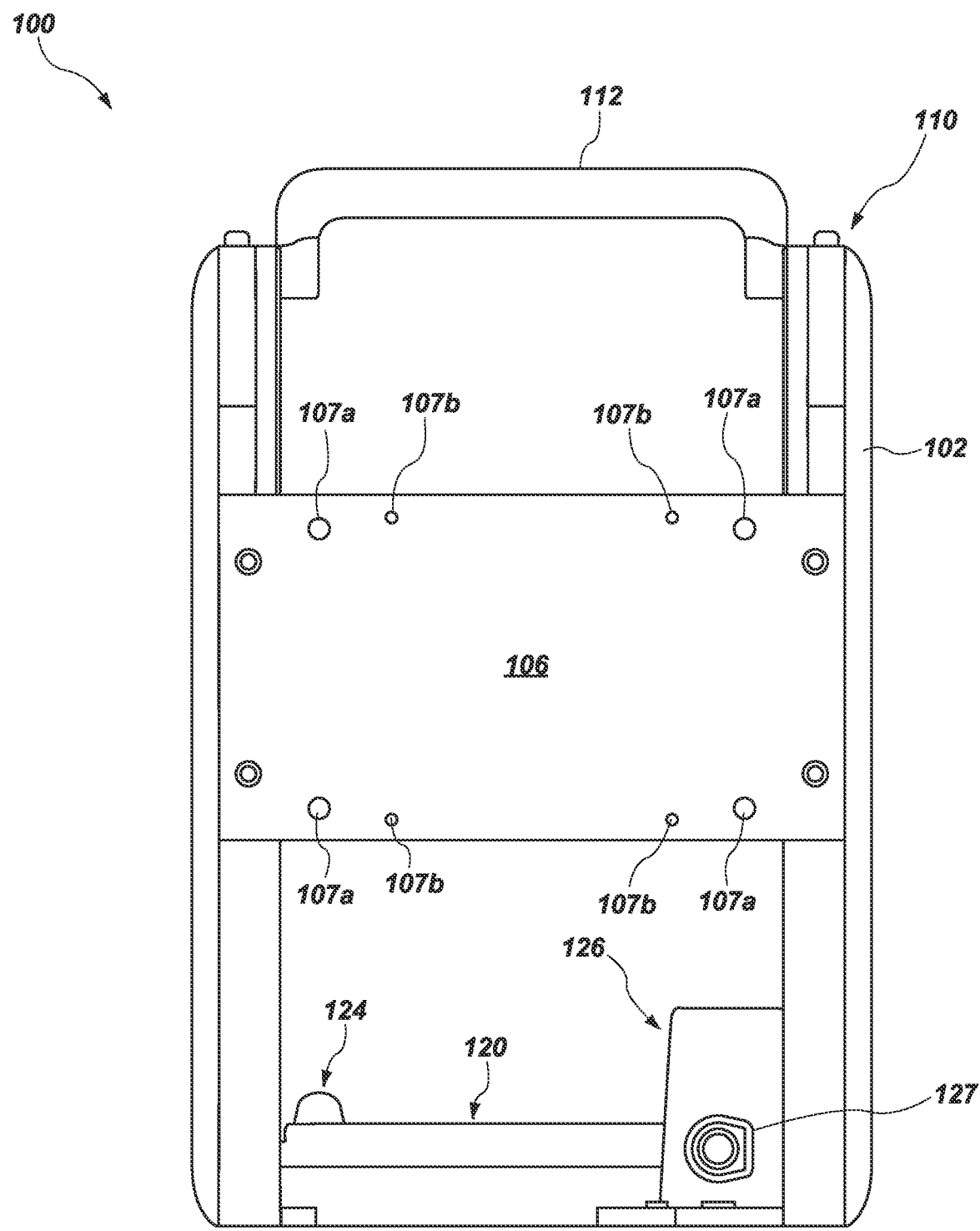
FIG. 5 illustrates a rear plan view of the example docking station depicted in FIG. 1.
Figure 6:
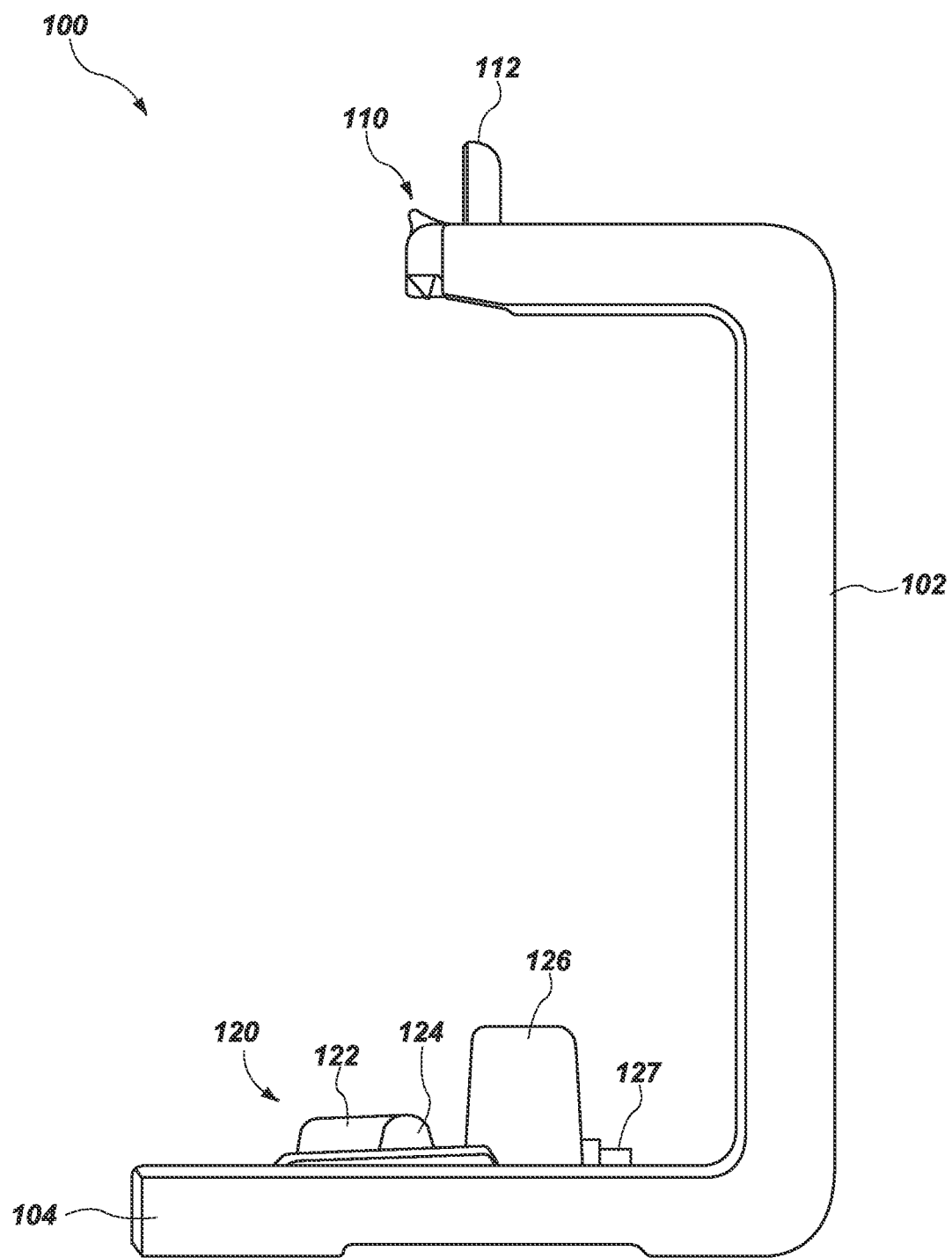
FIG. 6 illustrates a side plan view of the example docking station depicted in FIG. 1.

In some examples, the docking station 100 is configured to be mounted to a wall, cabinet, or other surface (e.g., a vertically-oriented surface) using the back plate 106. The back plate 106 include openings, such as the through holes 107a to allow the docking station 100 to be coupled to a vertical surface like a wall of an ambulance. In FIG. 5, for example, four through holes 107a defined in the back plate 106 are shown—an upper left through hole 107a, an upper right through hole 107a, a lower left through hole 107a, and a lower right through hole 107a. The through holes 107a defined in the back plate 106 are configured to receive fasteners, such as screws, nails, bolts, or other fasteners, and the fasteners pass through the through holes 107a to engage (e.g., fasten into) a vertical surface behind the docking station 100 to couple the docking station 100 to the vertical surface. In some examples, the vertical surface to which the docking station 100 is mounted includes mounting hardware, such as threaded openings to allow the fasteners to be passed through the through holes 107a and mounted to the mounting hardware of the vertical surface. In an example, the back plate 106 is configured to be coupled to the vertical surface, and then the frame 102 of the docking station 100 is configured to be coupled to the back plate 106. In another example, the back plate 106 is configured to be coupled to the frame 102 of the docking station 100, and then the docking station 100 is configured to be coupled to the vertical surface using the back plate 106.

In some examples, the back plate 106 includes features that engage complementary features of the vertical surface to couple the docking station 100 to the vertical surface. In an example, the vertical surface includes pins that protrude from the vertical surface, and the through holes 107a of the back plate 106 are configured to be placed onto the pins to mount the docking station 100 to the vertical surface. In another example, the vertical surface includes hooks onto which the back plate 106 is configured to be rested to mount the docking station 100 to the vertical surface.

Figure 12:
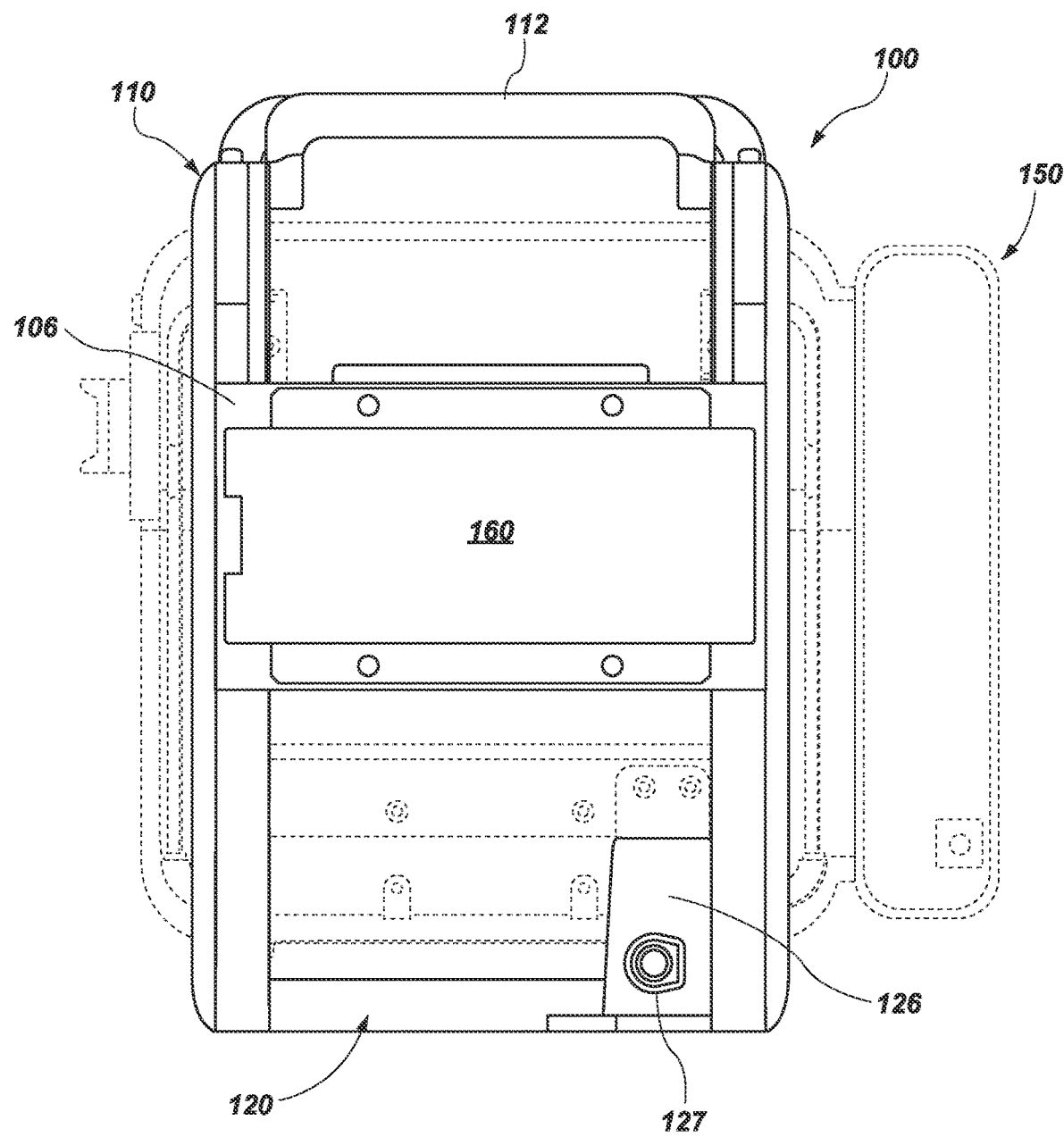
FIG. 12 illustrates a rear plan view of the example medical device and docking station depicted in FIG. 7.
Figure 13:
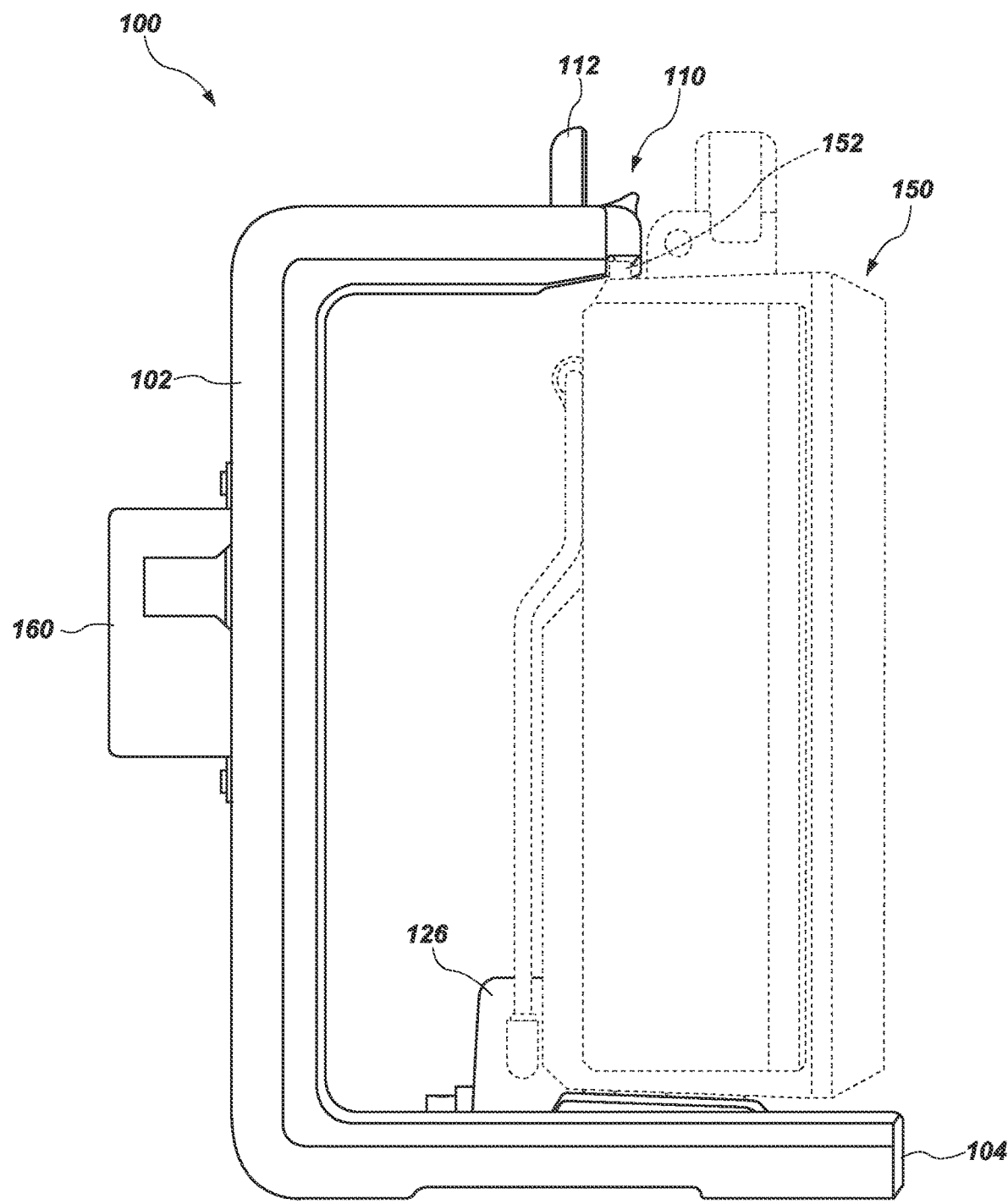
FIG. 13 illustrates a side plan view of the example medical device and docking station depicted in FIG. 7.
Figure 14:
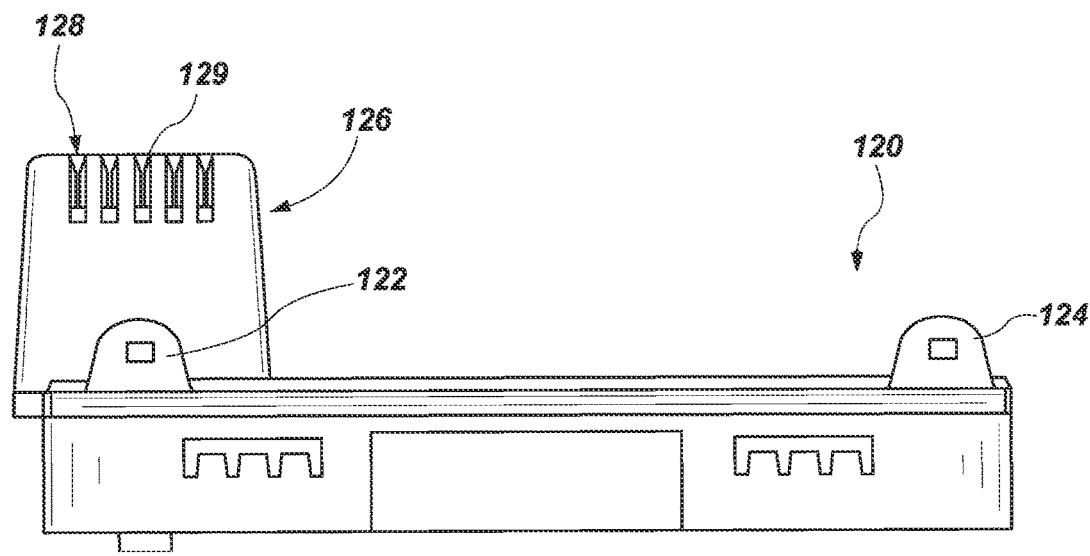
FIG. 14 illustrates a front plan view of an example base plate of a docking station.

In some examples, the through holes 107a, or other openings 107b, of the back plate 106 are configured to be used to couple accessories or modules, such as the accessory 160 shown in FIGS. 12 and 13, to the docking station 100. The accessory 160 is configured to be coupled to the back plate 106 using fasteners that engage or interface with the openings of the back plate 106. In some examples, the accessory 160 includes a communication module, a data transfer module, a power module, and/or another accessory, or a combination thereof. In some examples, the coupling of the accessory 160 to the back plate 106 is removable to allow the accessory 160 to be removed from the docking station 100. In some examples, the accessory 160 is configured to be coupled to the back plate 106 by means other than the openings 107a and/or 107b of the back plate 106. In some examples, the accessory 160 is configured to be coupled to a portion of the docking station 100 other than the back plate 106.

In the examples shown in FIGS. 1-13, the back plate 106 is coupled to the posts 102a of the frame 102. In some examples, the back plate 106 is configured to be coupled to one of the posts 102a of the frame 102, but not both of the posts 102a. In some examples, the frame 102 includes a single or multiple posts 102a, and the back plate 106 is configured to be coupled to some or all of the posts 102a of the frame 102. In these examples, the back plate 106 is also configured to be used to secure the docking station 100 to a surface, such as a vertical surface (e.g., a wall, a cabinet, etc.).

In some examples, rather than being coupled to a surface, the docking station 100 is configured to be portable or moveable. The docking station 100 is configured to rest on a surface and is movable or repositionable, as desired. In some examples, the legs 102c of the frame 102 of the docking station 100 include high-friction material (e.g., rubber) on their bottom surfaces to prevent movement, such as sliding, of the docking station 100 along or across the surface on which the docking station 100 rests.

Figure 3:
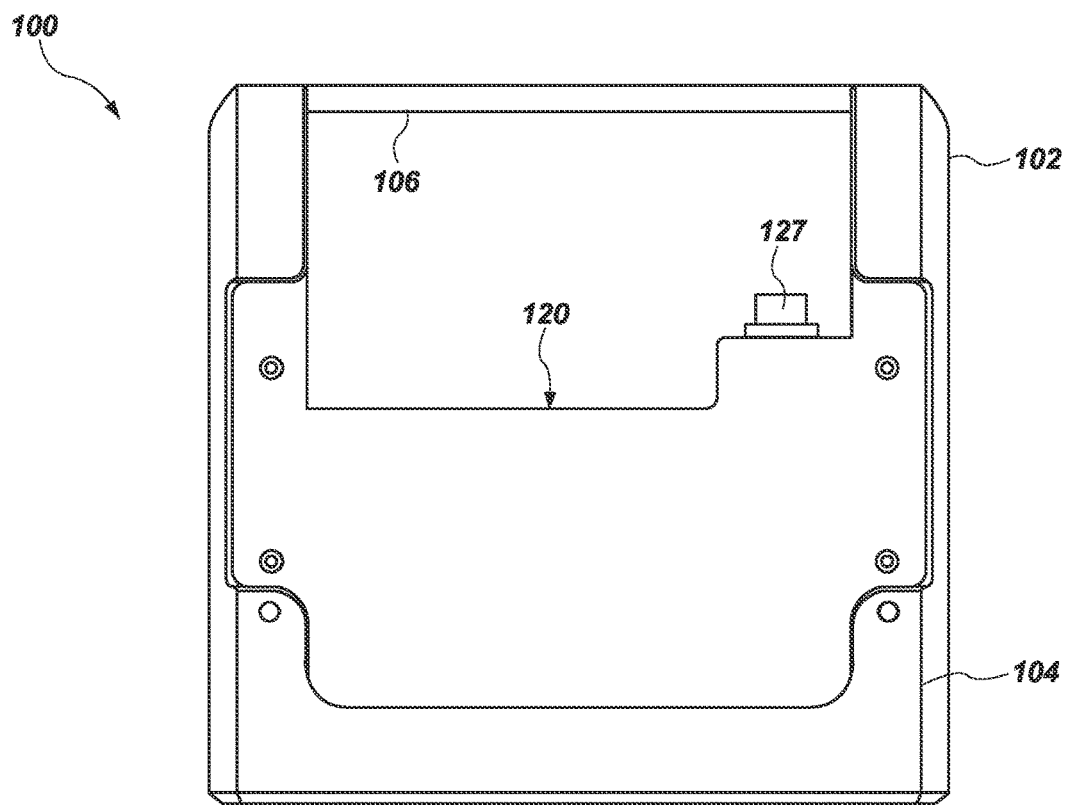
FIG. 3 illustrates a bottom plan view of the example docking station depicted in FIG. 1.
Figure 4:
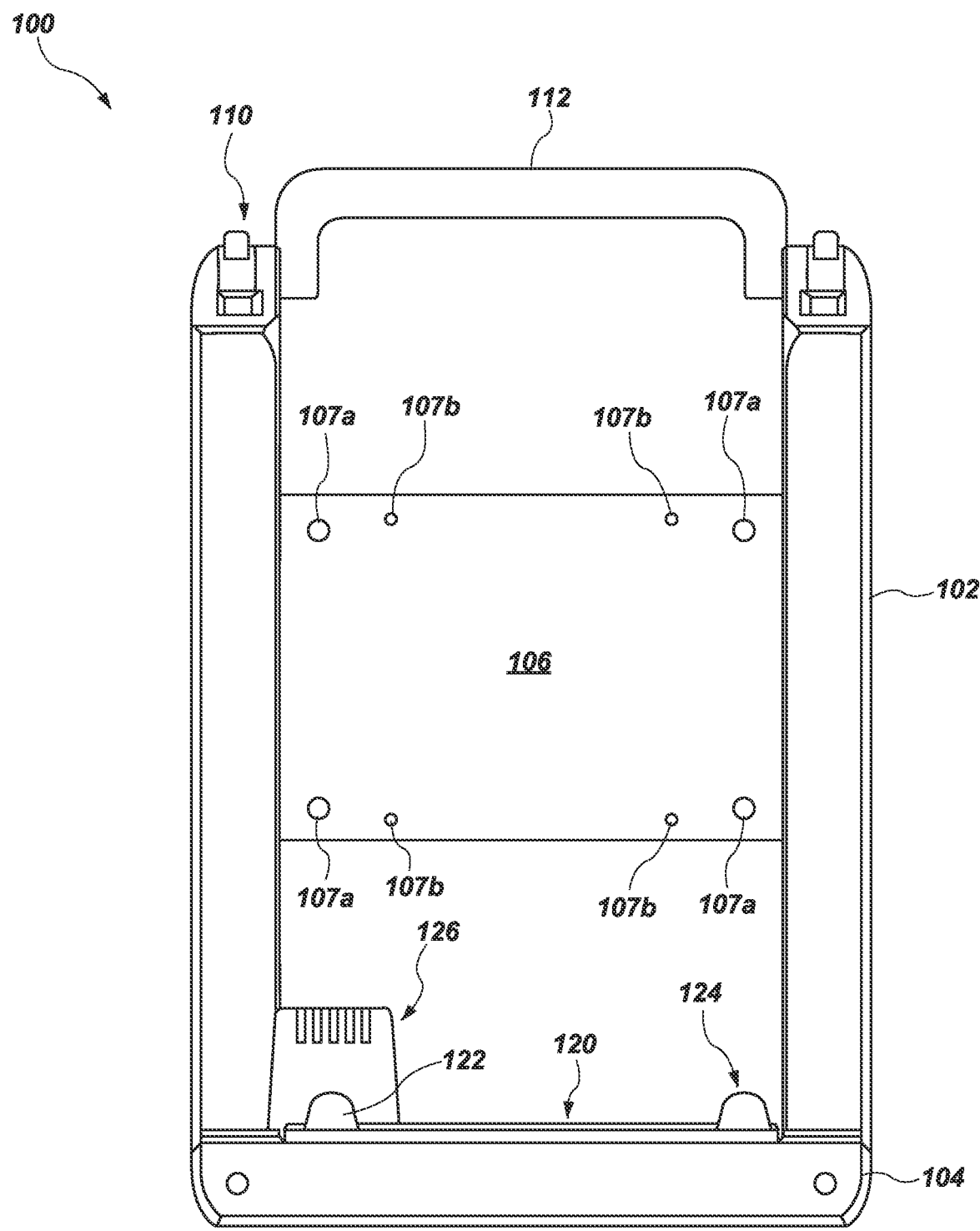
FIG. 4 illustrates a front plan view of the example docking station depicted in FIG. 1.

At least a portion of the base plate 120 is positioned between the legs 102c of the frame 102 of the docking station 100, as shown in FIG. 3. In some examples, the base plate 120 is configured to be coupled to the frame 102 by sliding the base plate 120 into slots defined in each of the legs 102c of the frame 102. In some examples, the slots are defined in the inner side surfaces, the top surfaces, and/or the bottom surfaces of the legs 102c to accommodate the base plate 120 and position the base plate 120 between the legs of the frame 102. The front plate 104 is configured to be coupled to the legs 102c of the frame 102 using fasteners, such as screws. In some examples, the front plate 104 is configured to be removably coupled to the legs 102c to retain the base plate 120 within the docking station 100. Removing the front plate 104 allows a rescuer to access to the base plate 120 so that the base plate 120 is accessible to be removed from the docking station 100. For example, removing the front plate 104 in FIG. 3 allows the rescuer to slide or manipulate the base plate 120 from between the legs 102c of the frame 102 of the docking station 100.

FIGS. 1, 4-6, and 14-16 show the base plate 120 with an external connector 127 to allow the electronic connector 126 to be electrically connected to an external device or system, such as a power source, communications system, or both (either by the same or two separate electrical connections). In this manner, when the medical device 150 is docked to the docking station 100, the medical device 150 is electrically connected to the electronic connector 126, and to the external device(s), network(s), or system(s) that are electrically connected to the base plate 120 by the external connector 127. The electrical connection of the medical device 150 to the external device(s), network(s), or system(s) allows the medical device 150 to receive power from an external source and/or to facilitate data communication and sharing of information and data between the medical device 150 and the external device(s), network(s), or system(s).

In an example, the docking station 100 is mounted within an ambulance or another type of emergency vehicle. A cable is electrically coupled to the external connector 127 of the base plate 120 at one end of the cable and is coupled to a power, data, or combined power and data connector within the vehicle on the other end of the cable. Since the docking station 100 is fixed in place, or is allowed to rotate on a turntable 130 that is fixed in place, this affixation of the docking station 100 to the vehicle acts as a strain relief on the cable that is connected to the vehicle and to the external connector 127 of the base plate 120, thereby preventing unintentional decoupling of the cable from the external connector 127 and/or the power and/or data connection within the vehicle so that the medical device 150 remains connected to the external device(s), network(s), or system(s). While the medical device 150 is docked to the docking station 100, there is an electronic connection between the medical device 150 and the electronic connector 126 of the base plate 120. This electrical connection allows the medical device 150 to receive electrical power from an external power source (e.g., a power source of the vehicle) and/or to communicate with the vehicle or another computing system(s) or network(s), such as the Internet.

To electrically connect the medical device 150 to the electronic connector 126 of the base plate 120, the rescuer docks the medical device 150 to the docking station 100. In some examples, to help position and orient the medical device 150 on the base plate 120, the base plate 120 includes positioning guides 122 and 124, such as shown in FIGS. 1, 4-6, and 14-16. The positioning guides 122 and 124 are shaped and sized to be engaged by (e.g., received within)

complimentary shaped and sized cavities defined in the bottom surface of the medical device 150.

In the example shown in FIGS. 1, 4-6, and 14-16, the positioning guide 122 is substantially oblong, is disposed on a top of the base plate, and is positioned along a first edge or side of the base plate 120 (e.g., left of the center of the base plate 120). The positioning guide 124 is substantially circular, is disposed on the top of the base plate, and is positioned along a second edge or side of the base plate 120 (e.g., right of the center of the base plate 120), which is opposite the first side. In some examples, both positioning guides 122 and 124 taper inwards from a base of each of the positioning guides 122, 124 towards a top surface of each of the positioning guides 122, 124. The inward taper of the positioning guides 122, 124 from the base to the top of the positioning guides 122, 124 helps align the complimentary cavities defined in the bottom surface (or base) of the medical device 150 with the positioning guides 122, 124. In doing so, the medical device 150 is easily oriented and positioned on the base plate 120 in the proper position and/or orientation as the medical device 150 is docked to the docking station 100. The ease and efficiency of placing the medical device 150 into or onto the docking station 100, at which point the medical device 150 is coupled to external power and/or communications, reduces the amount of time spent connecting the medical device 150 to power and/or to an external device(s) and/or system(s). In emergency situations, this docking efficiency allows the rescuer to more quickly return to focusing on the patient, because the rescuer does not have to separately connect the medical device 150 to external power and/or device(s) and/or system(s).

In some examples, the base plate 120 includes a different number of positioning guides, such as one positioning guide, or more than two positioning guides. In some examples, the positioning guides 122, 124 have different shapes or profiles, and/or the location(s) of the positioning guides 122, 124 on the base plate 120 differ from what is shown, or a combination thereof. In some examples, the base plate 120 does not include the positioning guides 122, 124.

FIGS. 7-13 illustrate various views of the medical device 150 docked to the docking station 100. The docking mechanism 110 of the docking station 100 engages a portion of the medical device 150, such as protrusions 152 extending from a top of the medical device 150 to dock the medical device 150 to the docking station 100. The protrusions 152 of the medical device 150 are located on the top surface of the medical device 150 and are sized, shaped and positioned on the top surface of the medical device 150 to be engaged (e.g., grasped, hooked, etc.) by hooks 116 of the docking mechanism 110. The handle 112 is configured to be actuated (e.g., rotated, pivoted, etc.) to raise the hooks 116 upwards and over the protrusions 152 of the medical device 150, which disengages the docking mechanism 110 from the medical device 150 and allows the rescuer to remove the medical device 150 from the docking station 100.

To use the docking station 100, the rescuer inserts the medical device 150 into, or places the medical device 150 onto, the docking station 100 in an arc trajectory. For examples, the rescuer initially positions the medical device 150 at an angled orientation with respect to the base plate 120 of the docking station 100, so that the base (or bottom surface) of the medical device 150 is positioned in the space between the arms 102b and the legs 102c of the frame 102. In this orientation, a front 150a of the medical device 150 is oriented towards the base plate 120 and/or the legs 102c, and a rear portion 150b of the medical device 150 is oriented towards the arms 102b of the frame 102. As the medical device 150 is further inserted into the docking station 100, the base (or bottom surface) of the medical device 150 contacts the base plate 120 along the front 150a of the medical device 150. The medical device 150 is then tilted backwards (or towards an upright orientation) so that the medical device 150 is brought into alignment with the posts 102a of the frame 102. As the medical device 150 is tilted along an arc pathway backwards, the base (or bottom surface) of the medical device 150 contacts a greater area of the base plate 120. By the rescuer continuing to rotate the medical device 150 backwards along the arc pathway, the base (or bottom surface) of the medical device 150 seats onto the positioning guides 122, 124 of the base plate 120, and the electronic connector 126 engages the mating electronic connector of the medical device 150.

In some examples, as the rescuer tilts the medical device 150 backwards along the arc pathway while docking the medical device 150, the protrusions 152 of the medical device 150 come into contact the hooks 116 disposed at the distal ends of a pair of docking arms 115 of the docking mechanism 110. This contact between the hooks 116 and the protrusions 152 of the medical device 150 forces the docking mechanism 110 into an open position, and it forces the hooks 116 of the docking arms 115 to be moved upwards and over the protrusion 152 of the medical device 150. The docking mechanism 110 is biased (e.g., by springs 114) to return to an engaged position once the medical device 150 is docked to the docking station 100, and this causes the docking mechanism 110 to engage (e.g., grasp, hook onto, etc.) the protrusions 152 of the medical device 150 when the hooks 116 moved past an edge (or ledge) of the protrusions 152. When the rescuer actuates (e.g., rotates, pivots, etc.) the handle 112 towards the monitor-defibrillator 152, the docking mechanism 110 moves into the open position and disengages from the protrusions 152 of the medical device 150 by the hooks 116 moving upwards and over the protrusions 152 of the medical device 150. When the docking mechanism 110 is in the open position, the medical device 150 is removable from the docking station 100.

Figure 9:
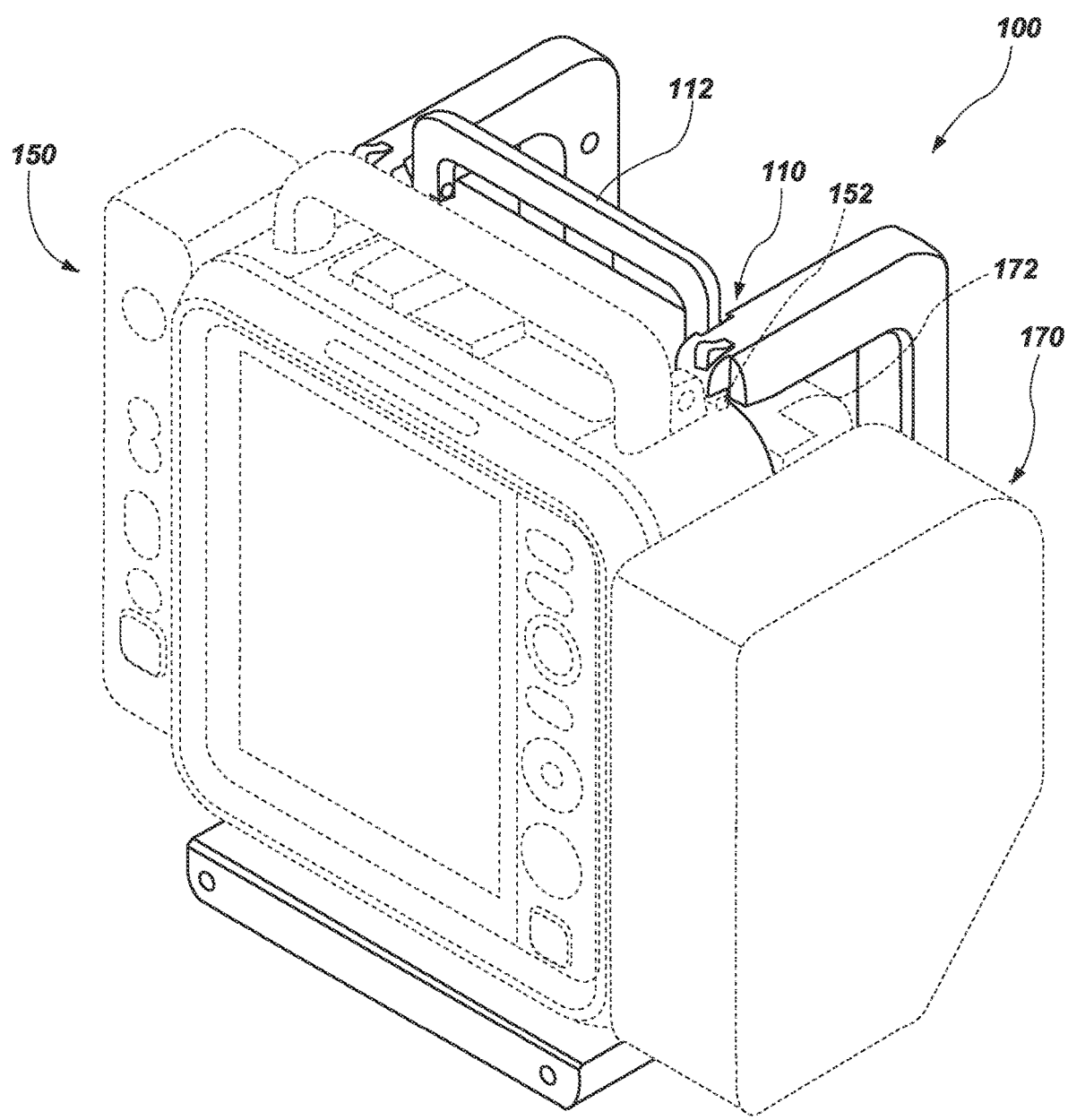
FIG. 9 illustrates a front perspective view of the example medical device and docking station depicted in FIG. 7 with example storage bags coupled to the medical device.

FIGS. 9 and 10 show the medical device 150 with storage bags 170 and 172 coupled to the medical device 150. The storage bags 170, 172 are configured to store various accessories, sensors, consumables, and/or other items that are configured to be used with the medical device 150 to assist with monitoring or treating the patient. The docking station 100 is shaped to allow the medical device 150 to be docked to the docking station 100 with the storage bags 170, 172 coupled to respective portions of the medical device 150 because there is sufficient space to accommodate the storage bags 170, 172 while the medical device 150 is docked to the docking station 100. For example, the arms 102b and legs 102c of the frame 102 of the docking station 100 extend orthogonally from the posts 102a of the frame 102 so that the medical device 150 and the rear storage bag 172 coupled to the back of the medical device 150 fits within the space between the arms 102b, the legs 102c, and the posts 102a of the frame 102 when the medical device 150 is docked to the docking station 100. Meanwhile, the side storage bag 170 coupled to a side of the medical device 150 is disposed outside of the C-shaped frame 102 and does not interfere with any portion of the frame 102 when the medical device 150 is docked to the docking station 100. Accordingly, the rescuer does not have to remove the storage bags 170, 172 from the medical device 150 prior to docking the medical device 150 to the docking station 100, which allows the rescuer to efficiently dock the medical device 150 to the docking station 100 and remove the medical device 150 from the docking station 100 with the storage bags 170, 172 coupled to the medical device 150. In this manner, supplies and accessories are easily and efficiently transported with the medical device 150 to a patient needing care.

Figure 15:
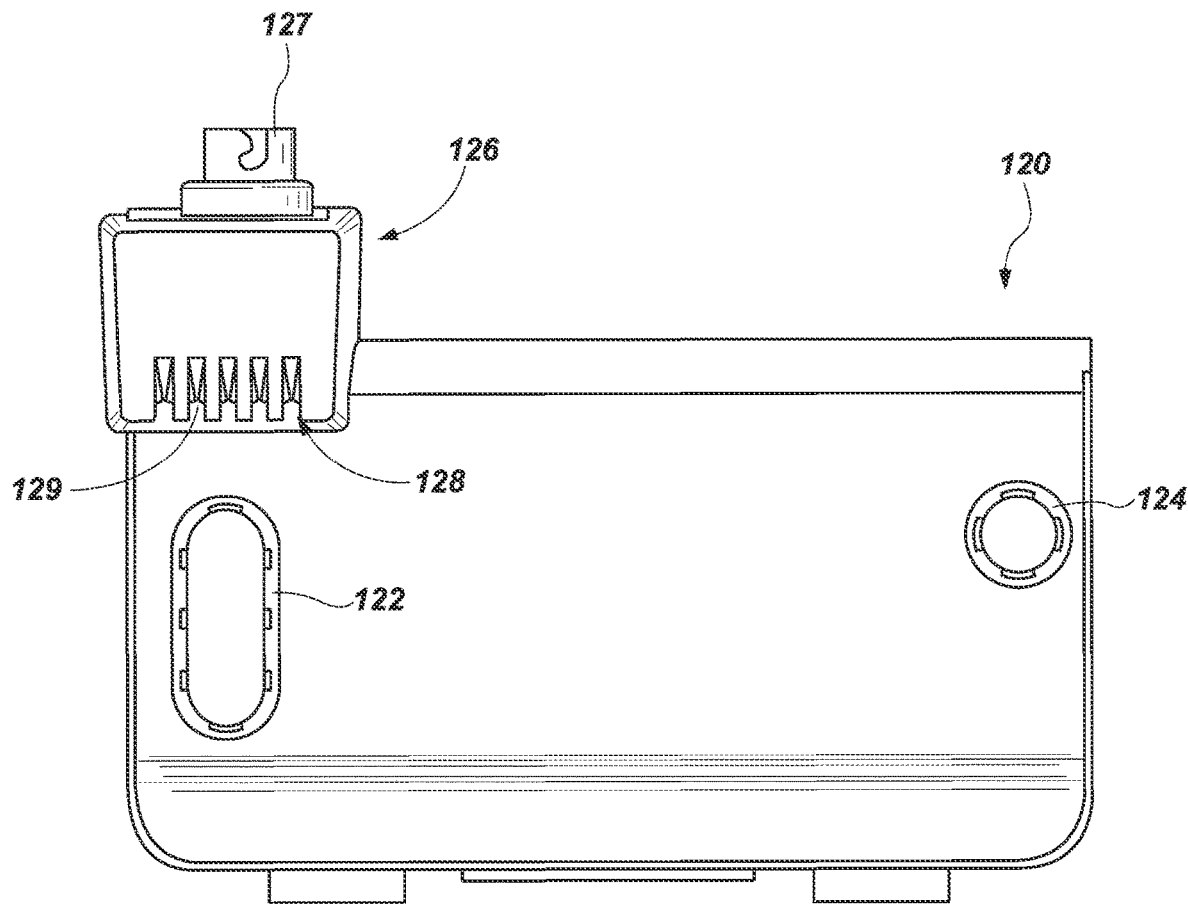
FIG. 15 illustrates a top plan view of the example base plate depicted in FIG. 14.
Figure 16:
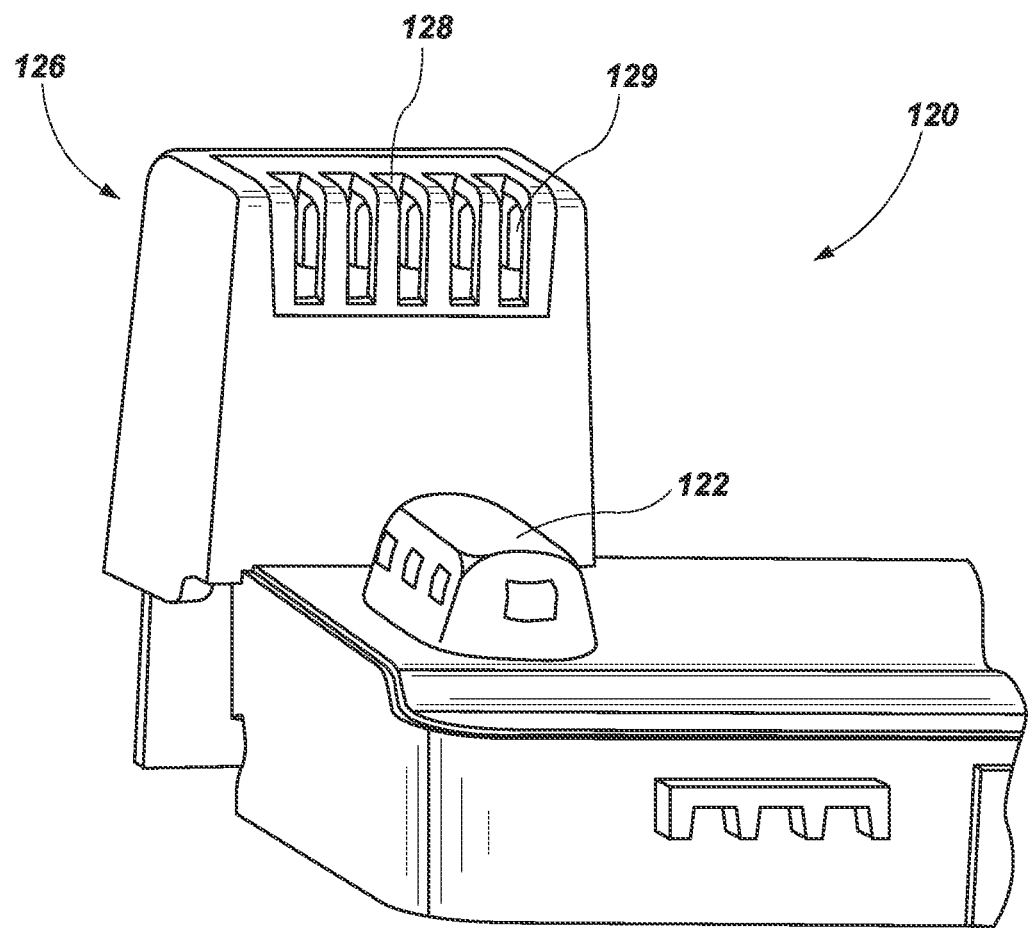
FIG. 16 illustrates a perspective view of a portion of the base plate depicted in FIG. 14.
Figure 17:
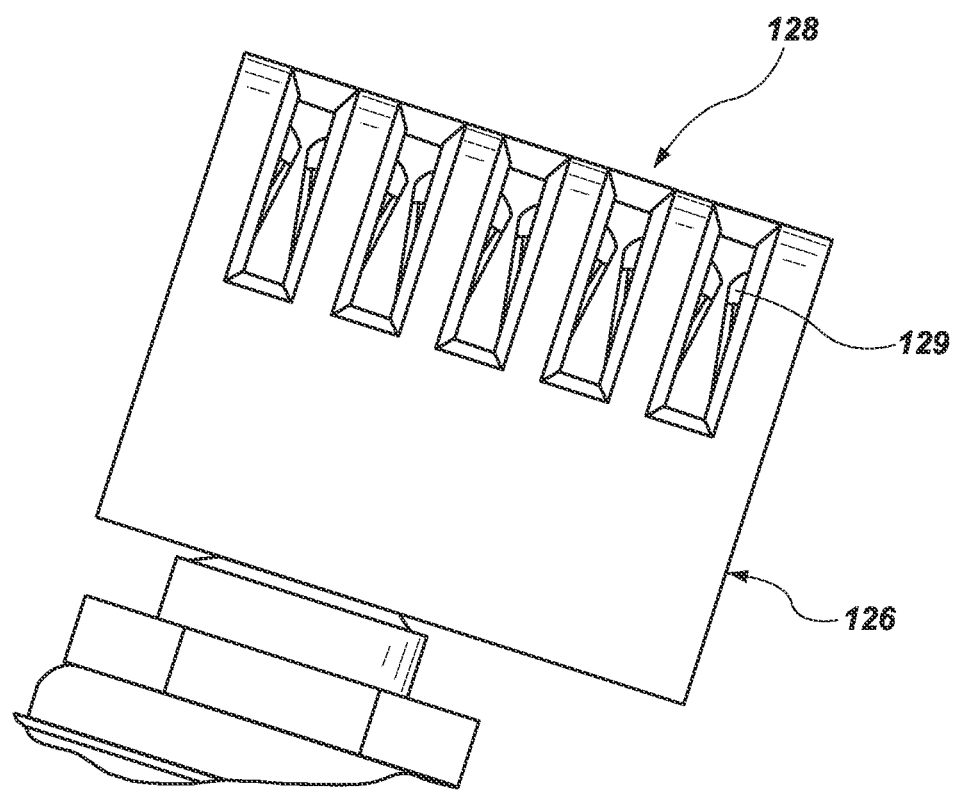
FIG. 17 illustrates a top view of an example integrated connector of the example base plate depicted in FIG. 14.

As shown in FIGS. 15-17, the base plate 120 includes the positioning guides 122, 124 and the electronic connector 126. The electronic connector 126 has multiple slots 128 that defined in the top and front surfaces of the electronic connector 126. The slots 128 are open and continuous across both a portion of the top surface and the front surface of the electronic connector 126. The slots 128 are evenly spaced apart in this example, although the spacing between the slots 128 can vary in alternative examples. Each of the slots 128 include spring-like electrical contacts 129 that each have two sides which are biased towards the center of a slot due to the spring-like nature. This allows the electrical contacts 129 to engage and form an electrical connection with portions of an electronic connector of the medical device 150 that are inserted within the slots 128. In other examples, some, but not all, of the slots 128 include an electrical contact 129. In still other examples, the electrical contacts 129 are contacts for the same electrical connection, such as the power supply, or the electrical contacts 128 include electrical connections for two or more different electronic connections, such as a combination of the power supply, a communication connection, and/or other types of connections.

In some examples, the electronic connector 126 of the base plate 120 is configured to be coupled to an external device or system, such as a power source, a communication system, or both, by a cable coupled to the external connector 127 of the electronic connector 126. This coupling via the external connector 127 allows the medical device 150 to draw power from an external source, transfer data to/from an external device(s) and/or system(s), or both when the medical device 150 is docked to the docking station 100 and thereby electrically connected to the electronic connector 126 of the base plate 120. In an example, when the medical device 150 is electrically connected to the electronic connector 126, the medical device 150 automatically draws power from an external source to power the medical device 150 to charge one or more batteries of the medical device 150. In this manner, the one or more batteries of the medical device 150 are automatically charged and maintained in a substantially charged state so that the medical device 150 is ready for use as a portable device by removing the medical device 150 from the docking station 100. In some examples, the medical device 150 is configured to communicate information to the external device(s), network(s), or system(s), such as operating data, historical patient treatment data, status information, physiological data of the patient being monitored, and/or other data using the cable connected to the external connector 127 of the electronic connector 126. In some examples, the external device(s), network(s), or system(s) are configured to transfer data to the medical device 150 when the medical device 150 is docked to the docking station 100. For example, an external device(s), network(s), or system(s) are configured to provide software updates to the medical device 150, communicate information to the rescuer operating the medical device 150 (e.g., by outputting information via an output device of the medical device 150, such as a display, speakers, a printer, etc.), or other information or data to the medical device 150.

The mating electronic connector of the medical device 150 that is configured to couple to the electronic connector 126 of the base plate 120 is positioned on the back 150b of the medical device 150, such as near the lower-right corner of the back 150b of the monitor-defibrillator. The positioning of the mating electronic connector of the medical device 150 allows the mating electronic connector to engage the electronic connector 126 of the base plate 120 when the medical device 150 is docked to the docking station 100. The mating electronic connector of the medical device 150 includes blade- or planar-shaped electrical contacts that are sized, spaced, and positioned to engage (e.g., insert into) the slots 128 of the electronic connector 126 of the base plate 120. When the medical device 150 is docked to the docking station 100, the blade-shaped electrical contacts of the mating electronic connector are inserted into the slots 128 and physically contact the electrical contacts 129 of the electronic connector 126 to complete one or more electrical connections between the medical device 150 and the electronic connector 126 of the docking station 100.

In some examples, the mating electronic connector of the medical device 150 is configured to be positioned anywhere on the medical device 150 (e.g., at the top of the back 150b, at a bottom left corner of the back 150b, etc.). Accordingly, the electronic connector 126 is configured to be positioned on the docking station 100 at a position where the electronic connector 126 engages the mating electronic connector of the medical device 150 when the medical device 150 is docked to the docking station 100. In some examples, the interface between the electronic connector 126 of the docking station 100 and the mating electronic connector of the medical device 150 is different than the described blade-shaped electrical contacts. In an example, the mating electronic connector of the medical device 150 includes one or more circular conductors that interface with an electronic connector 126 having complimentary shaped circular receptacles, or vice versa.

In the configuration where the mating electronic connector of the medical device 150 includes blade-shaped electrical contacts and the electronic connector 126 includes slots 128, an electrical connection is able to be established or broken quickly, without the rescuer having to perform a complex or difficult task other than docking the medical device 150 to or removing the medical device 150 from the docking station 100. The efficiency of the electronic connection between the medical device 150 and the electronic connector 126 helps minimize delays in patient monitoring and/or treatment using the medical device 150.

In some examples, the medical device 150 is removed from the docking station 100 using a similar arc trajectory used to dock the medical device 150 to the docking station 100, but in reverse. It is to be appreciated that a sudden interruption of the electrical connection between the medical device 150 and the electronic connector 126 can cause the medical device 150 to have operating inefficiencies, such as errors caused by the sudden interruption of communication and/or power connection between the medical device 150 and an external device(s), network(s), or system(s). To minimize such inefficiencies, the medical device 150, in some examples, is configured to detect an imminent disconnection of the medical device 150 from the electronic connector 126.

In an example, one of the blade-shaped electrical contacts of the mating electronic connector of the medical device 150 is shorter and/or smaller than the other, remaining blade-shaped electrical contacts of the mating electronic connector. During decoupling of the medical device 150 from the docking station 100, the electrical connection between the shorter and/or smaller blade-shaped contact and an associated electrical contact 129 of the electronic connector 126 is broken before the electrical connections between the other, remaining blade-shaped electrical contacts and the associated electrical contacts 129 of the electronic connector 126. The interruption of the electrical connection between the smaller blade-shaped contact and the corresponding electrical contact 129 of the electronic connector 126 is sensed or detected by the medical device 150 as an indication that the electrical connection between the medical device 150 and the electronic connector 126 is about to be interrupted. The interruption of the electrical connection between the smaller blade-shaped contact and the corresponding electrical contact 129 occurs before the interruption of the electrical connection between the longer and/or larger, remaining blade-shaped contacts and the remaining electrical contacts 129 because the medical device 150 is removed along an arced pathway, which forces the disconnection of the smaller-blade connection before the longer-blade connections are disconnected. Thus, the medical device 150 detects that one of the electrical contacts 129 is no longer coupled to a corresponding blade-shaped contact of the mating electronic connector, the medical device 150 determines that the electrical connection is about to be interrupted, and the medical device 150 performs one or more operations to prepare for the interruption of the electrical connection, and the electrical connection between the other, larger blade-shaped contacts of the mating electronic connector and the remaining electrical contacts 129 of the electronic connector 128 are usable until the interruption of the electrical connection due to the removal of the medical device 150 from the docking station 100. For example, the medical device 150 completes a data transfer and/or provides an indication that the data transfer is about to be interrupted so that the recipient of data being transferred is able to properly process or interpret the transferred data and prepare for an impending interruption (e.g., by saving data to memory, saving a progress point of the data transfer process, etc.). In some examples, in response to the imminent data interruption, the medical device 150 stores the data in memory for later transfer and prevents the data from being overwritten until the data is able to be transferred for processing, storage or both.

Figure 7:
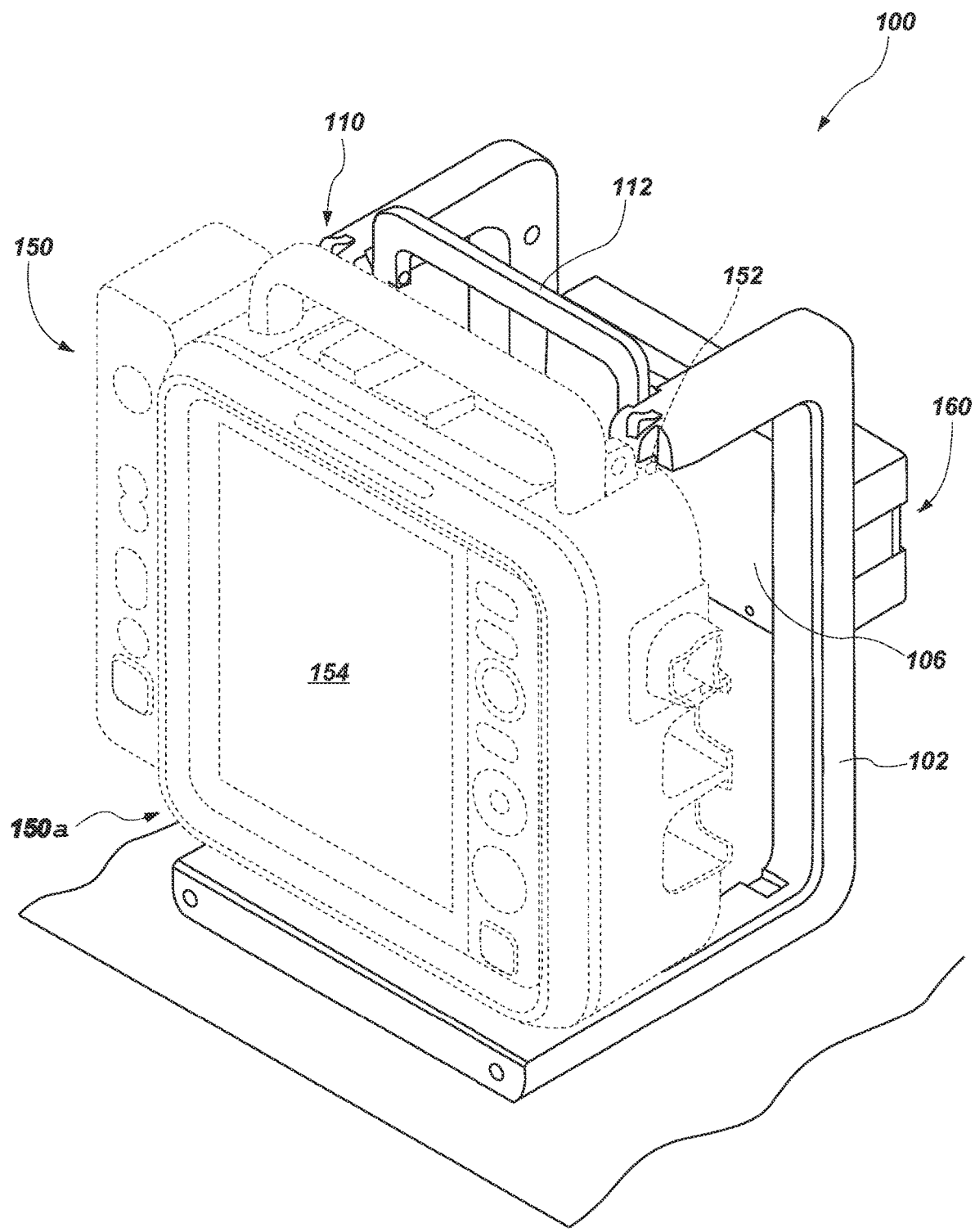
FIG. 7 illustrates a front perspective view of a medical device docked to the example docking station depicted in FIG. 1.
Figure 8:
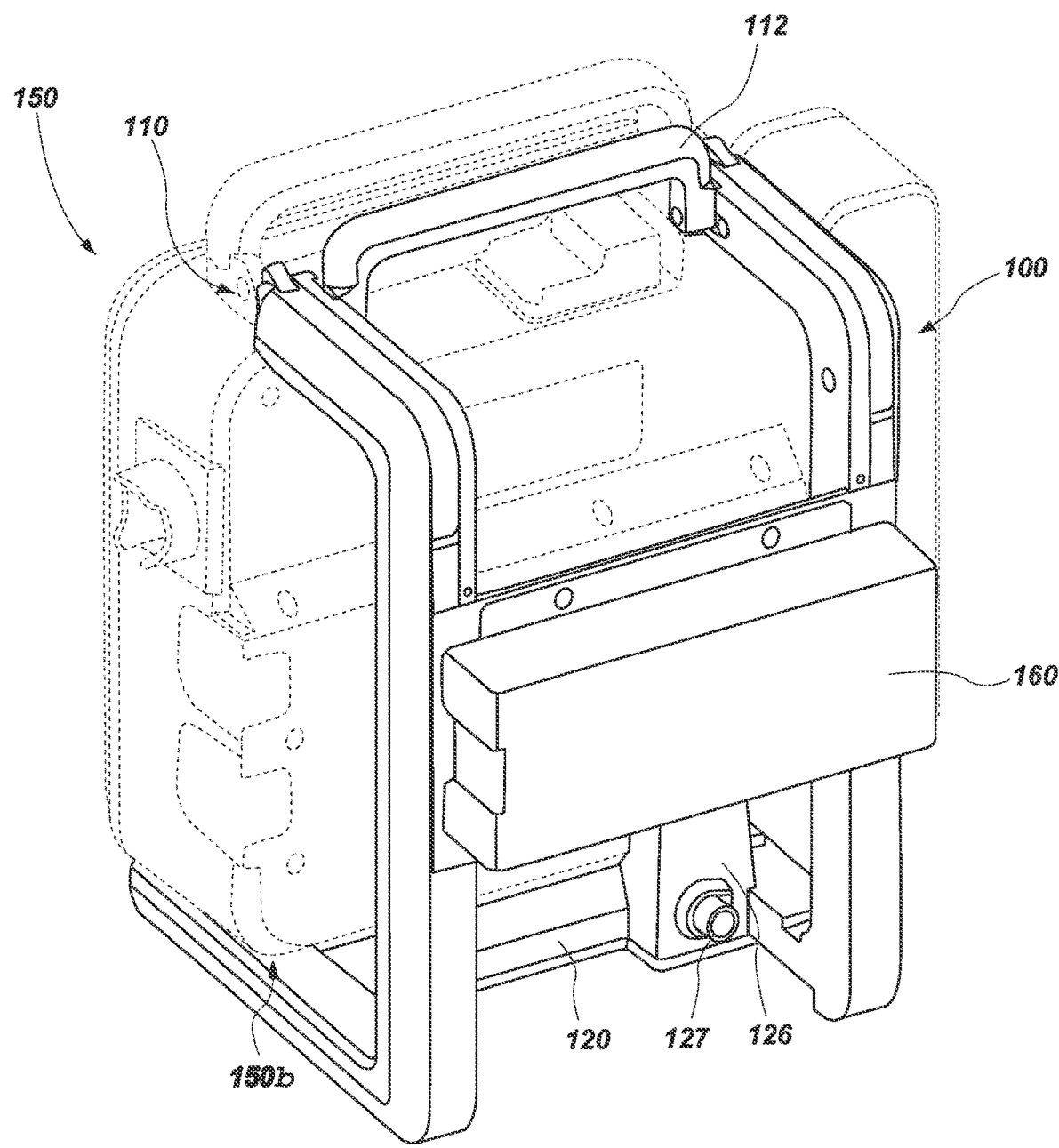
FIG. 8 illustrates a rear perspective view of the example medical device and docking station depicted in FIG. 7.

In another example, the medical device 150 alters or changes its configuration in response to detecting the imminent disconnection from the power connection, data connection, or both. In this example, the medical device 150 includes a touchscreen 154, such as shown in FIG. 7, which is configured to display a user interface that includes various information regarding the patient and allows the rescuer to access various functions of the monitor-defibrillator 120 (e.g., by interacting through touching user interface elements on the touchscreen 154). The touchscreen 154 is configured to display different user interfaces depending on the situation, such as a docked user interface and an undocked user interface, depending on whether the medical device 150 is docked to the docking station 100 or is removed therefrom. The medical device 150 is configured to automatically switch between the docked and undocked user interfaces, such as switching to the undocked user interface in response to detecting the imminent disconnection from the electronic connector 126. The docked user interface is catered to monitoring or treating the patient while the patient is being transported (e.g., in an emergency vehicle), and the undocked user interface is catered to monitoring or treating a patient at a location, such as a rescue scene or operation. The various user interface configurations are customizable, and/or the user interface configuration is automatically selected and used in response to the imminent disconnection from the electronic connector 126. This allows the rescuer to configure the docked and undocked user interfaces of the medical device 150 according to user preferences, such as allowing the rescuer to position patient information on the touchscreen 154 and to access the functions of the medical device 150 by positioning user interface elements on the touchscreen 154 at the rescuer's preferred positions. In some examples, the docked and undocked user interfaces of the medical device 150 are different depending on the type of medical device. For example, the docked and undocked user interfaces of the medical device 150 display different information or provide the rescuer different capabilities than the docked and undocked user interfaces of a different type of medical, such as an AED or other medical device. By being able to detect the imminent disconnection of the medical device 150 from the electronic connector 126, the medical device 150 is able to configure itself automatically to better assist the rescuer and also minimize or prevent inefficiencies, such as incomplete data transfers, loss of generated data that had not yet been stored and/or transferred, and the like that otherwise affects the usability of the medical device 150.

Figure 18:
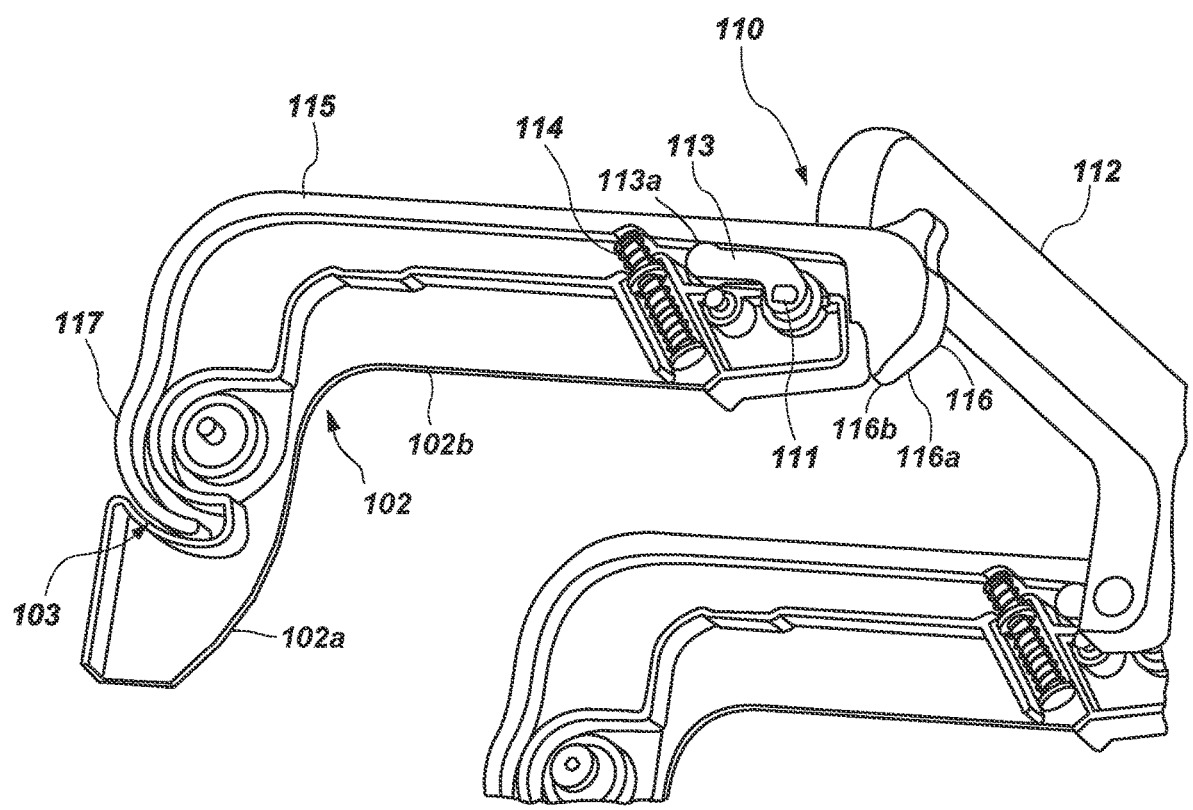
FIG. 18 illustrates a cutaway view of an example docking mechanism of a docking station.

FIG. 18 is a cutaway view of a portion of the frame 102 of the docking station 100. The cutaway view shows various components of the docking mechanism 110 within one of the arms 102b of the frame 102. The other arm 102b of the frame 102 includes similar components in a similar and mirrored arrangement. The docking arm 115 is positioned substantially along the center of the arm 102b of the frame 102. The docking arm 155 includes a hook 116 that extends beyond the arm 102b of the frame 102 at a distal end of the arm 102b. The docking arm 155 also includes a retained portion 117 that is received and/or disposed within a recess 103 defined in the rear of the post 102a of the frame 102. The retained portion 117 of the docking arm 115 is movable into and out of the recess 103, which allows the docking arm 115 to rotate and move the hook 116 upwards. The handle 112 is positioned between the arms 102b of the frame 102 and includes an axle 111 at either end of the handle 112. The axle 111 extends into the arm 102b of the frame 102 and engages a cam 113 within the arm of the frame 102. A free end 113a of the cam 113 is rounded and contacts an underside of the docking arm 115 within the arm 102b of the frame 102. When a rescuer rotates the handle 112 towards the front of the docking station 100, the free end 113a of the cam 113 is rotated upwards within the arm 102b of the frame 102, which lifts or raises the docking arm 115. The upward movement of the docking arm 115 causes the hook 116 to move upwards, and the retained portion 117 to rotate within and move further into the recess 103. The upward movement of the hook 116 caused by the rotation of the handle 112 disengages the hook 116 from the protrusions 152 of the medical device 150 to allow the medical device 150 to be removed from the docking station 100.

FIG. 18 shows a spring 114 that is coupled to the underside of the docking arm 115 and configured to bias the docking arm 115 to return to a resting position within the arm 102b of the frame 102. In some examples, the spring 114 is disposed around a stud of the docking arm 115 to counter the motion of the stud and bias the docking arm 115 towards the resting position. In the resting position, the hook 116 is in its lowermost position and engages (e.g., grasps, hooks, grabs, etc.) one of the protrusions 152 of the medical device 150 when the medical device 150 is docked to the docking station 100. When the hook 116 engages one of the protrusions 152, the medical device 150 is docked to the docking station 100.

The hook 116 of the docking arm 115 includes a sloped face 116a that tapers to a point 116b of the hook 116. The sloped face 116a of the hook 116 is configured to contact a protrusion 152 of the medical device 150 and to move upwards when the medical device 150 is docked to the docking station 100. This is due to the sloped face 116a sliding along and over the protrusion 152 as the medical device 150 is docking. Once the protrusion 152 passes beyond the point 116b of the hook 116, the hook 116 is no longer sliding along the protrusion 152 and the hook 116 moves downwards to engage the protrusion 152 due to the bias of the spring 114 that causes the docking arm 115 to return to the resting position. In this manner, the rescuer does not have to rotate the handle 112 when placing the medical device 150 into the docking station 100 and, instead, pushes the protrusions 152 of the medical device 150 under and beyond the hooks 116 of the docking mechanism 110 to dock the medical device 150 to the docking station 100.

Example Clauses

1. A docking station for a defibrillator, the docking station including: a frame including: a first C-shaped member including: a first post that is vertically-oriented when the docking station is upright; a first arm extending orthogonally from a top of the first post; and a first leg extending orthogonally from a bottom of the first post; and a second C-shaped member including: a second post that is vertically-oriented when the docking station is upright; a second arm extending orthogonally from a top of the first post; and a second leg extending orthogonally from a bottom of the first post; and a base plate coupled to the frame, wherein at least a portion of the base plate is positioned between the first leg and the second leg, and wherein the base plate is configured to contact a base of the defibrillator and to support the defibrillator when the defibrillator is docked to the docking station.

2. The docking station of clause 1, further including an electronic connector integrated with the base plate and configured to couple to the defibrillator and to provide power originating from an external power source to the defibrillator when the defibrillator is docked to the docking station.

3. The docking station of clause 2, wherein the electronic connector is further configured to couple the defibrillator to an external device for allowing transmission of data between the defibrillator and the external device.

4. The docking station of any one of clauses 1 to 3, further including a docking mechanism coupled to the frame, wherein at least a portion of the docking mechanism is positioned between the first arm and the second arm, the docking mechanism including a pair of hooks that are configured to engage a pair of protrusions disposed on a top of the defibrillator when the defibrillator is docked to the docking station.

5. The docking station of clause 4, wherein the docking mechanism includes a handle that is configured to be actuated, wherein actuation of the handle causes the pair of hooks to disengage from the pair of protrusions to remove the defibrillator from the docking station.

6. The docking station of any one of clauses 1 to 5, further including a back plate coupled to the first post and the second post, the back plate being usable to mount the docking station to a vertical surface or to couple an accessory to the backplate.

7. The docking station of any one of clauses 1 to 6, further including a turntable coupled to the base plate or to the first leg and the second leg, the turntable configured to allow the docking station to rotate relative to a surface on which the docking station rests.

8. A docking station for a defibrillator, the docking station including: a frame including: a pair of posts that are vertically-oriented when the docking station is upright; and a pair of legs extending orthogonally from bottoms of the pair of posts; and a base plate coupled to the frame, wherein at least a portion of the base plate is positioned between the pair of legs, and wherein the base plate is configured to contact a base of the defibrillator and to support the defibrillator when the defibrillator is docked to the docking station.

9. The docking station of clause 8, further including an electronic connector disposed on the base plate and configured to couple to the defibrillator and to provide power originating from an external power source to the defibrillator when the defibrillator is docked to the docking station.

10. The docking station of clause 9, wherein the electronic connector is further configured to couple to a cable that supplies the power originating from the external power source.

11. The docking station of any one of clauses 8 to 10, further including a docking mechanism coupled to the frame, wherein the frame further includes a pair of arms extending orthogonally from tops of the pair of posts, and wherein at least a portion of the docking mechanism is positioned between the pair of arms at distal ends of the pair of arms, the docking mechanism including a pair of hooks that are configured to engage a pair of protrusions disposed on a top of the defibrillator when the defibrillator is docked to the docking station.

12. The docking station of clause 11, wherein the docking mechanism includes a handle that is configured to be actuated, wherein actuation of the handle causes the pair of hooks to disengage from the pair of protrusions to remove the defibrillator from the docking station.

13. The docking station of any one of clauses 8 to 12, further including a back plate coupled to the pair of posts, the back plate being usable to mount the docking station to a vertical surface or to couple an accessory to the backplate.

14. The docking station of any one of clauses 8 to 13, further including a turntable coupled to the base plate or to the pair of legs, the turntable configured to allow the docking station to rotate relative to a surface on which the docking station rests.

15. A docking station for a defibrillator, the docking station including: a frame including: a middle portion that is vertically-oriented when the docking station is upright; an upper portion disposed at a top of the middle portion; and a lower portion disposed at a bottom of the middle portion; and a base plate coupled to the frame at the lower portion, the base plate configured to contact a base of the defibrillator and to support the defibrillator when the defibrillator is docked to the docking station.

16. The docking station of clause 15, further including an electronic connector disposed on the base plate and configured to couple to the defibrillator and to provide power originating from an external power source to the defibrillator when the defibrillator is docked to the docking station.

17. The docking station of clause 15 or 16, further including a docking mechanism coupled to the upper portion of the frame, the docking mechanism including a pair of hooks that are configured to engage a pair of protrusions disposed on a top of the defibrillator when the defibrillator is docked to the docking station.

18. The docking station of clause 17, wherein the docking mechanism includes a handle that is configured to be actuated, wherein actuation of the handle causes the pair of hooks to disengage from the pair of protrusions to remove the defibrillator from the docking station.

19. The docking station of any one of clauses 15 to 18, further including a back plate coupled to the middle portion of the frame, the back plate being usable to mount the docking station to a vertical surface or to couple an accessory to the backplate.

20. The docking station of any one of clauses 15 to 19, further including a turntable coupled to the base plate or to the lower portion of the frame, the turntable configured to allow the docking station to rotate relative to a surface on which the docking station rests.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A system comprising:
a defibrillator; and
a docking station for the defibrillator, the docking station comprising:
a base plate configured to contact a base of the defibrillator and to support the defibrillator when the defibrillator is docked to the docking station; and
an electronic connector integrated with the base plate,
wherein, when the defibrillator is docked to the docking station, a mating electronic connector of the defibrillator connects to the electronic connector to establish an electrical connection, and
wherein the defibrillator is configured to:
detect an imminent disconnection of the defibrillator from the electronic connector; and
perform an operation in response to detecting the imminent disconnection and prior to an interruption of the electrical connection.

2. The system of claim 1, wherein:
the mating electronic connector comprises a plurality of electrical contacts;
an electrical contact of the plurality of electrical contacts is shorter than remaining electrical contacts of the plurality of electrical contacts;
when the defibrillator is being removed from the docking station, a second electrical connection between the electrical contact and a corresponding electrical contact of the electronic connector is interrupted before electrical connections between the remaining electrical contacts and corresponding electrical contacts of the electronic connector are interrupted; and
the defibrillator is configured to detect the imminent disconnection by sensing an interruption of the second electrical connection.

3. The system of claim 1, wherein performing the operation comprises completing a data transfer.

4. The system of claim 1, wherein:
the defibrillator comprises a touchscreen configured to display at least a first user interface when the defibrillator is docked to the docking station and a second user interface when the defibrillator is removed from the docking station; and performing the operation comprises switching to the second user interface.

5. The system of claim 4, wherein:
the first user interface is catered to monitoring or treating a patient being transported in an emergency vehicle; and
the second user interface is catered to monitoring or treating the patient at a rescue scene.

6. The system of claim 1, wherein:
the base plate comprises positioning guides comprising at least a first positioning guide and a second positioning guide;
each positioning guide is configured to mate with a corresponding cavity defined in the base of the defibrillator, thereby positioning the defibrillator relative to the base plate; and
a first shape of the first positioning guide is different than a second shape of the second positioning guide.

7. The system of claim 1, wherein:
the docking station further comprises a frame; and
the base plate is coupled to the frame at a lower portion of the frame.

8. The system of claim 7, wherein the frame is C-shaped.

9. A medical device comprising:
a first electronic connector positioned on a back of the medical device; and
a base configured to be supported by a base plate of a docking station when the medical device is docked to the docking station,
wherein, when the medical device is docked to the docking station, the first electronic connector connects to a second electronic connector integrated with the base plate of the docking station, and
wherein the medical device is configured to:
detect an imminent disconnection of the medical device from the second electronic connector; and
perform an operation in response to detecting the imminent disconnection.

10. The medical device of claim 9, wherein:
the first electronic connector comprises a plurality of electrical contacts;
an electrical contact of the plurality of electrical contacts is smaller than remaining electrical contacts of the plurality of electrical contacts;
when the medical device is being removed from the docking station, an electrical connection between the electrical contact and a corresponding electrical contact of the second electronic connector is interrupted before electrical connections between the remaining electrical contacts and corresponding electrical contacts of the second electronic connector are interrupted; and
the medical device is configured to detect the imminent disconnection by sensing an interruption of the electrical connection.

11. The medical device of claim 9, wherein performing the operation comprises altering a configuration of the medical device.

12. The medical device of claim 9, wherein performing the operation comprises performing multiple operations comprising:
storing data in memory; and
preventing the data from being overwritten until the data is transferred for processing.

13. The medical device of claim 9, further comprising a touchscreen configured to display at least a first user interface when the medical device is docked to the docking station and a second user interface when the medical device is removed from the docking station, wherein performing the operation comprises switching to the second user interface.

14. The medical device of claim 9, wherein the medical device is a defibrillator.

15. The medical device of claim 9, further comprising cavities defined in the base and configured to receive positioning guides of the base plate, wherein the positioning guides have different shapes.

16. A method comprising:
establishing, by a medical device, an electrical connection based on a connection between an electronic connector of a docking station and a mating electronic connector of the medical device;
detecting, by the medical device, an imminent disconnection of the medical device from the electronic connector; and
performing, by the medical device, an operation in response to the detecting and prior to an interruption of the electrical connection.

17. The method of claim 16, wherein the performing comprises completing a data transfer.

18. The method of claim 16, wherein the performing comprises providing an indication that a data transfer is about to be interrupted.

19. The method of claim 16, wherein the performing comprises switching from displaying a first user interface via a touchscreen of the medical device to displaying a second user interface via the touchscreen.

20. The method of claim 16, wherein:
the mating electronic connector comprises a plurality of electrical contacts;
an electrical contact of the plurality of electrical contacts is shorter than remaining electrical contacts of the plurality of electrical contacts; and
the detecting comprises sensing, by the medical device, an interruption of a second electrical connection between the electrical contact and a corresponding electrical contact of the electronic connector.

* * * * *